United States Patent
Wells et al.

(10) Patent No.: US 10,154,842 B2
(45) Date of Patent: Dec. 18, 2018

(54) THROUGH THE SCOPE TENSION MEMBER RELEASE CLIP

(75) Inventors: Brian Keith Wells, LaGrange, KY (US); Lance Alan Wolf, Madison, AL (US); Gregory R. Furnish, Louisville, KY (US); Vasiliy P. Abramov, Louisville, KY (US); William C. Mers Kelly, Crestwood, KY (US); Russell F. Durgin, Attleboro, MA (US); Theresa A. Durgin, legal representative, Bellingham, MA (US); Gary A. Jordan, Litchfield, NH (US); Allison Kidder, Boston, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1646 days.

(21) Appl. No.: 13/463,560

(22) Filed: May 3, 2012

(65) Prior Publication Data
US 2013/0123807 A1   May 16, 2013

Related U.S. Application Data

(60) Provisional application No. 61/482,429, filed on May 4, 2011.

(51) Int. Cl.
*A61B 17/08* (2006.01)
*A61B 17/10* (2006.01)

(52) U.S. Cl.
CPC .......... *A61B 17/083* (2013.01); *A61B 17/08* (2013.01); *A61B 17/10* (2013.01)

(58) Field of Classification Search
CPC ........ A61B 17/08; A61B 17/10; A61B 17/083
USPC ................................................ 606/142, 158
See application file for complete search history.

(56) References Cited

U.S. PATENT DOCUMENTS

| | | | |
|---|---|---|---|
| 2002/0133178 A1* | 9/2002 | Muramatsu et al. | 606/142 |
| 2002/0177861 A1* | 11/2002 | Sugiyama et al. | 606/151 |
| 2006/0155308 A1* | 7/2006 | Griego | 606/142 |
| 2010/0312259 A1* | 12/2010 | Houser et al. | 606/142 |

FOREIGN PATENT DOCUMENTS

| | | |
|---|---|---|
| DE | 10 2009 022 271 | 11/2010 |
| EP | 1 829 489 | 9/2007 |

* cited by examiner

*Primary Examiner* — Elizabeth Houston
*Assistant Examiner* — Tin Nguyen
(74) *Attorney, Agent, or Firm* — Fay Kaplun & Marcin, LLP

(57) ABSTRACT

An apparatus for deployment of a hemostatic clip includes a clip assembly releasably coupled to a distal portion of a shaft, wherein the clip assembly includes a capsule releasably coupled to the shaft, clip arms slidably received within the capsule and cooperating with the capsule to provide a first user feedback indicating a decision configuration of the clip assembly and a yoke slidably received within the capsule, the yoke including proximal and distal portions releasably and rotatably connected to one another via a first control wire, a distal end of the distal portion being connected to proximal ends of the clip arms. A second control wire extends from the handle assembly and is coupled to a proximal end of the second portion to move the clip assembly between open and closed configurations.

18 Claims, 25 Drawing Sheets

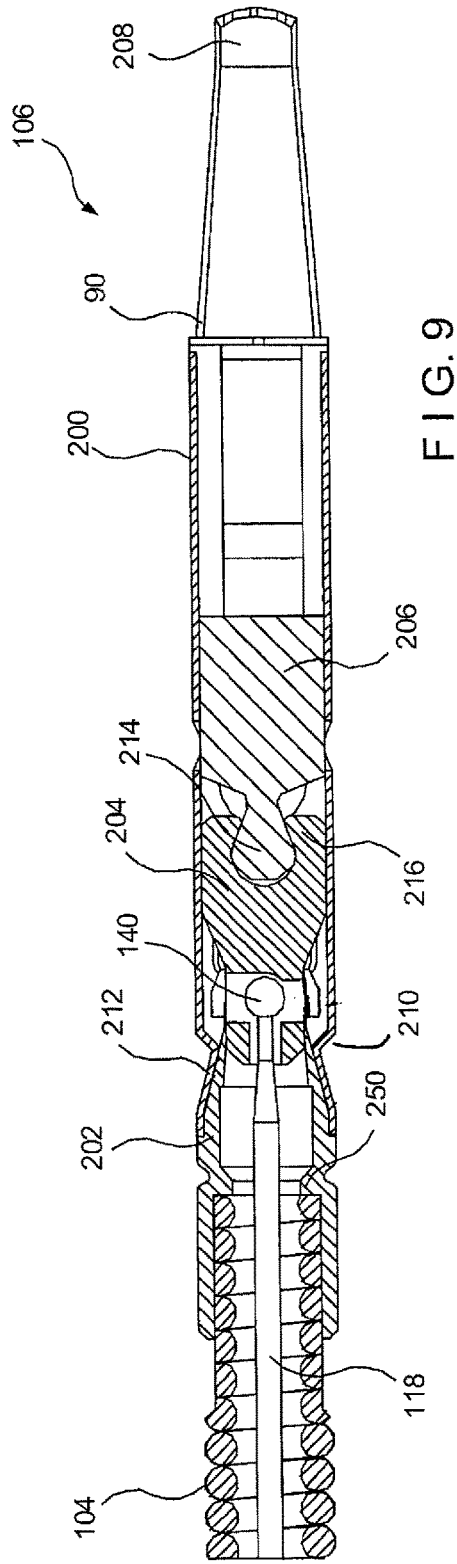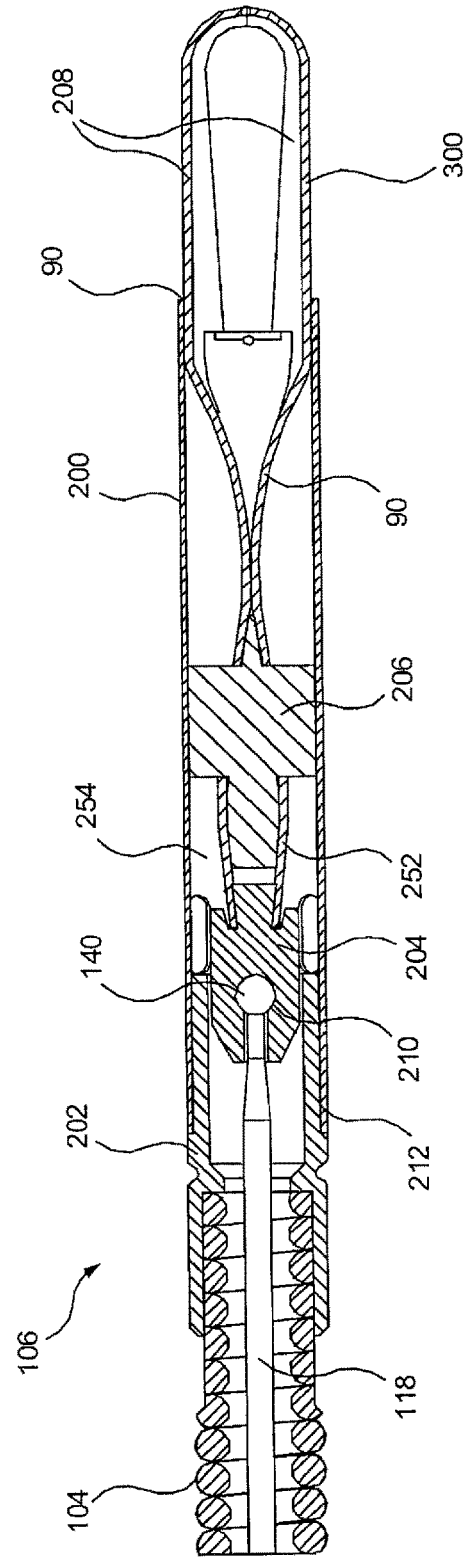

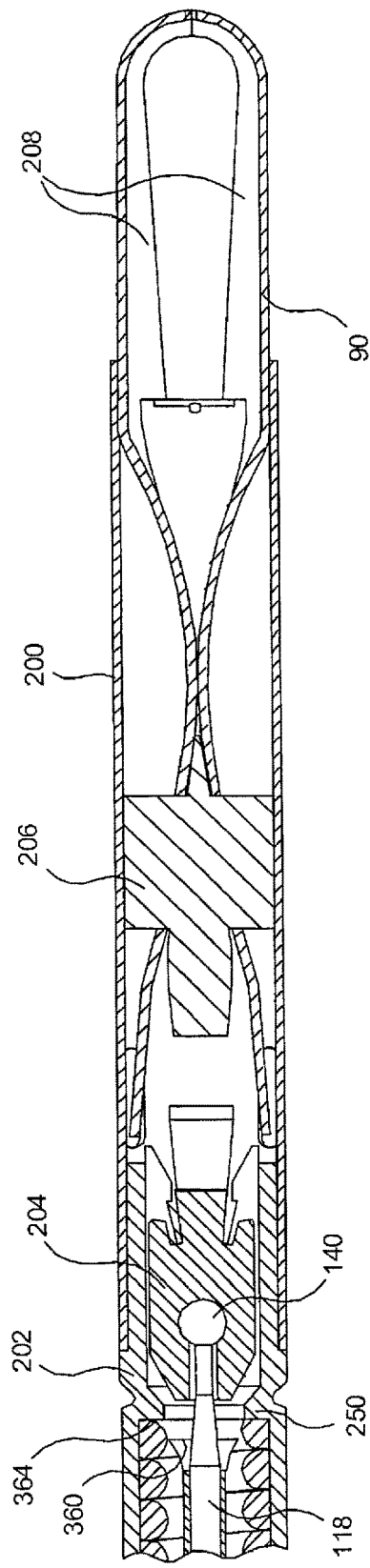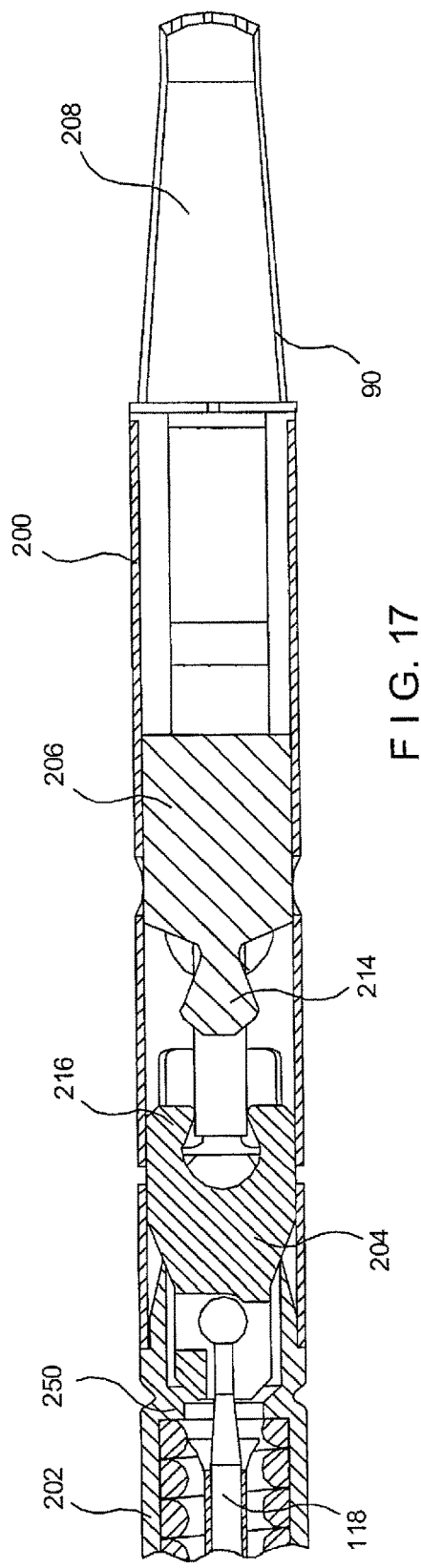

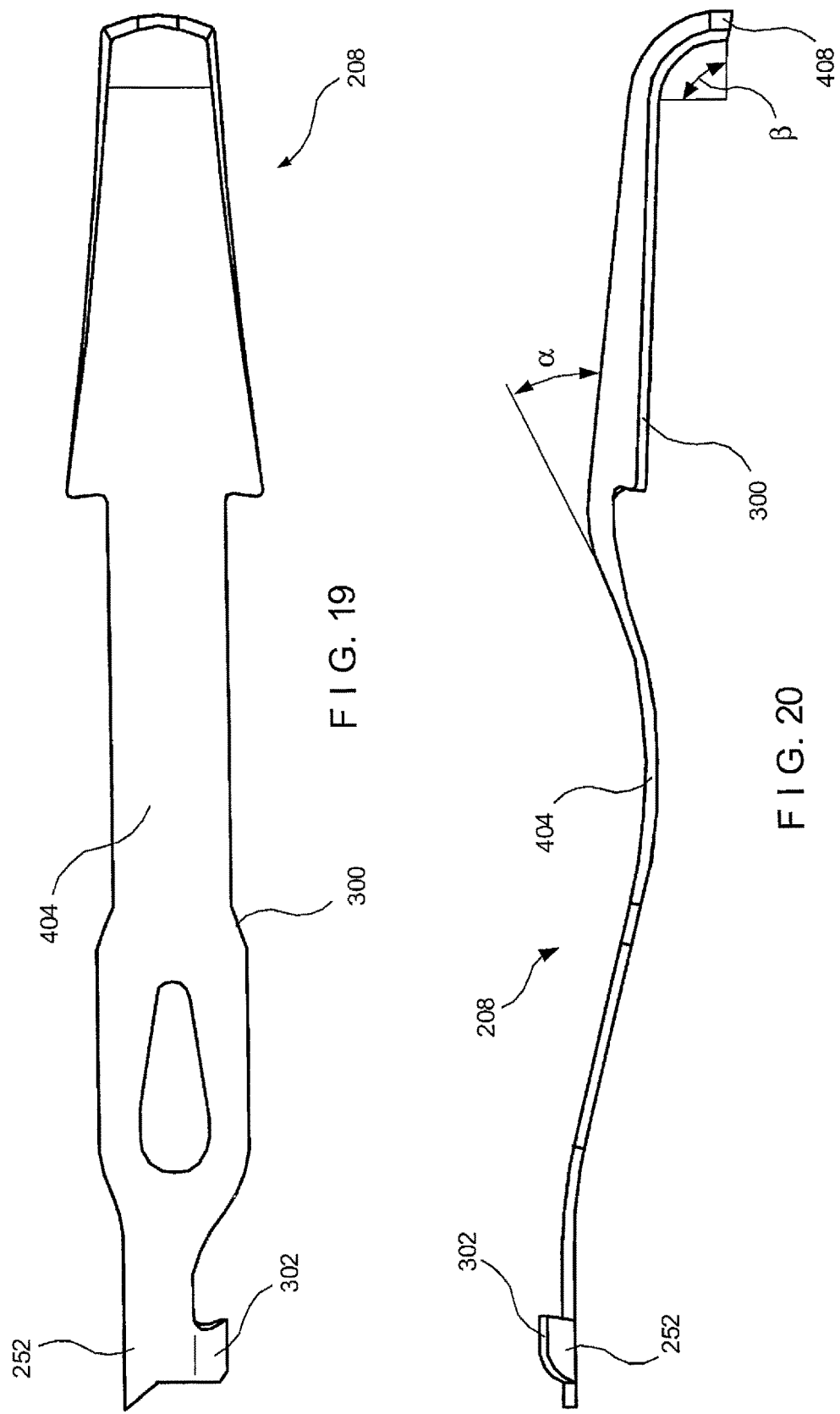

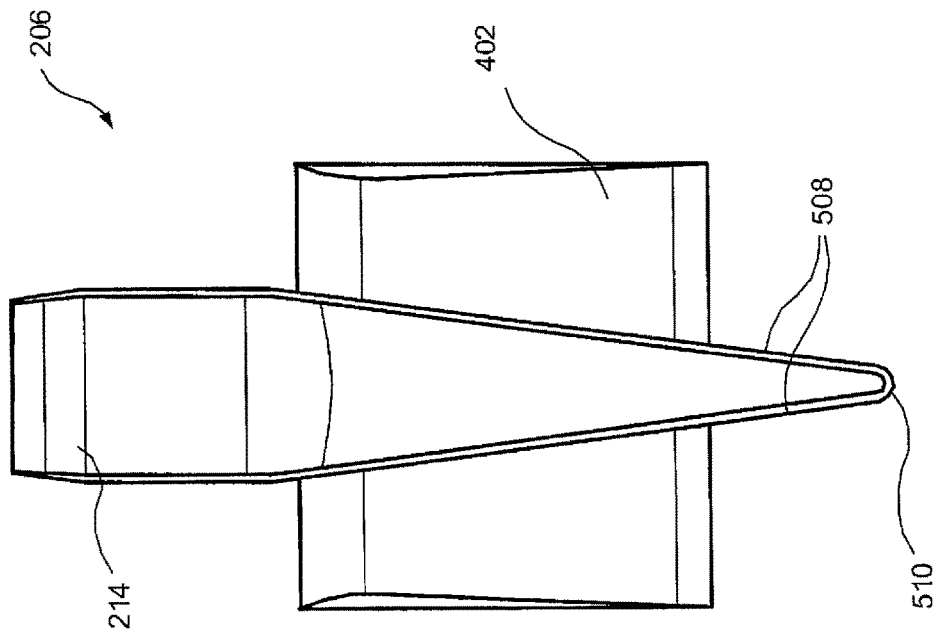
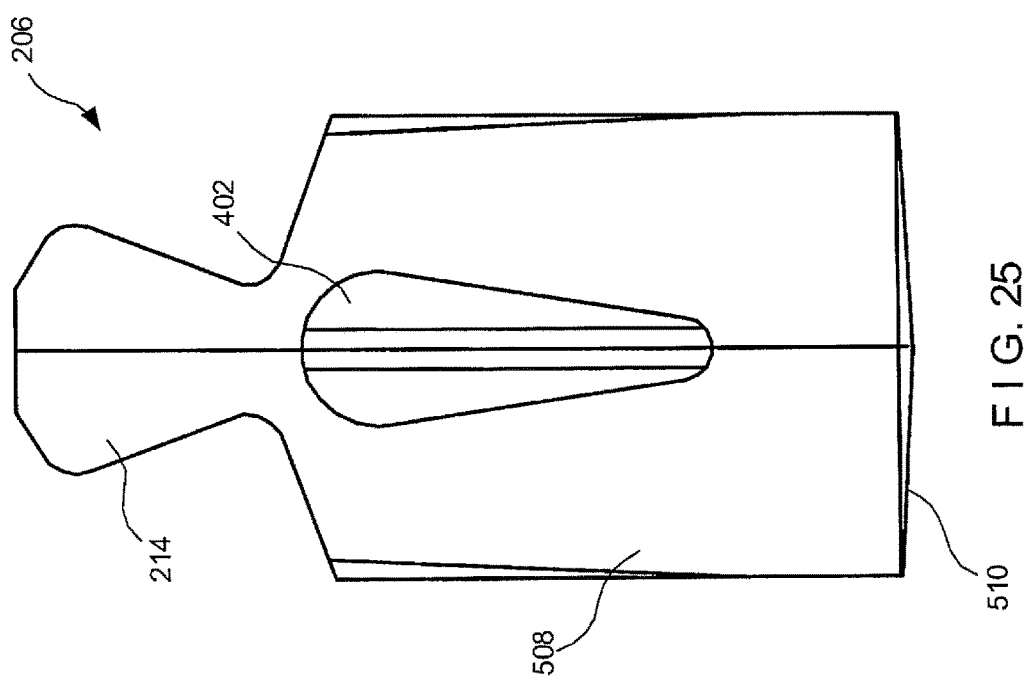

THROUGH THE SCOPE TENSION MEMBER RELEASE CLIP

PRIORITY CLAIM

The application claims the priority to the U.S. Provisional Application Ser. No. 61/482,429, entitled "Through the Scope Tension Member Release Clip" filed May 4, 2011. The specification of the above-identified application is incorporated herewith by reference.

BACKGROUND INFORMATION

Endoscopic procedures to treat abnormal pathologies of the gastro-intestinal ("GI") canal system, of the biliary tree, of the vascular system and of various other body lumens are becoming increasingly common. The endoscope is basically a hollow tube that is placed at a desired location within the body to facilitate access to the relevant body ducts and lumens, etc. The endoscope itself cannot carry out many of the required procedures. To that end, the endoscope is fitted with a lumen, or internal channel, which permits the user to insert various medical devices therethrough to the location that requires treatment. Once the distal end of the inserted device has reached the tissue to be treated, it can be manipulated using controls which remain outside the body.

An hemostatic clipping tool is one of the devices which may be inserted through an endoscope so that treatment may be carried out. Hemostatic clips are deployed from the clipping tool and are used to stop internal bleeding by clamping together the edges of a wound. The clipping tool complete with clips attached to its distal end is inserted through the endoscope to the location of the bleeding. A clip is then remotely manipulated into position over the site of bleeding, clamped over the wound and detached from the tool. After a number of clips sufficient to stop the bleeding has been deployed, the tool is withdrawn from the patient's body through the endoscope. The size and shape of the clips and of the clipping tool are limited by the inner diameter of the endoscope's lumen, thus placing constraints on the design of the clip positioning and release mechanisms.

One challenge facing the endoscope operator is to properly position the hemostatic clips over the wound, so that closing the clips over the tissue will be effective in stopping the bleeding. If a clip is deployed improperly, additional clips may be required to stop the bleeding extending the time required for and the complexity of the procedure and leaving additional medical devices within the patient. It is also important for the device operator to be certain of the status of the clip during the deployment operation. For example, before withdrawing the tool from the endoscope, the operator should have positive indication that a clip has fully deployed, and has been released from the tool. At the same time the design of the tool should ensure that clips are fully released after they have been closed over the tissue.

SUMMARY OF THE INVENTION

In one aspect, the present invention is directed to an apparatus for deployment of a hemostatic clip comprising a handle assembly and a shaft connected to a distal portion of the handle assembly in combination with a clip assembly releasably coupled to a distal portion of the shaft, the clip assembly including clip arms and a capsule cooperating with the clip arms to provide a first user feedback indicating a decision configuration of the clip assembly and a control wire including a ball connector, the control wire extending from the handle assembly and coupled to the clip assembly by the ball connector to maintain the clip assembly coupled to the shaft, wherein the ball connector is detachable from the clip assembly to provide a second user feedback indicating separation of the clip assembly from the shaft.

In a different aspect, the present invention is directed to a clip assembly deployable through an endoscope, comprising a capsule releasably connected to a bushing of an elongated clip deployment device, clip arms slidable within the capsule between a distal open configuration and a proximal closed configuration, a tension member slidable with the clip arms, urging the clip arms in the open configuration, and a yoke slidable within the capsule, releasably connected to the tension member at one end, and connected to a control wire of the clip deployment device at another end. In the invention, distal movement of the control wire slides the clip arms in the open configuration, and proximal movement of the control wire slides the clip arms in the closed configuration.

In a further embodiment, the invention is directed to a method for hemostatic clipping through an endoscope. The method includes providing a shaft section connected to a clip assembly of a clipping device insertable through an endoscope working lumen, providing a handle assembly attached to the shaft section, the handle assembly allowing longitudinal movement of a control wire, and providing a connection between a distal end of the control wire and clip arms of the clip assembly, whereby longitudinal movement of the control wire moves the clip arms between an open and a closed configuration. The method also includes giving a first user feedback indicating a decision configuration of the clip assembly, and giving a second user feedback indicating separation of the clip assembly from the shaft section.

The present invention is further directed to an apparatus for deployment of a hemostatic clip comprising a clip assembly releasably coupled to a distal portion of a shaft, wherein the clip assembly includes a capsule releasably coupled to the shaft, clip arms slidably received within the capsule and cooperating with the capsule to provide a first user feedback indicating a decision configuration of the clip assembly and a yoke slidably received within the capsule, the yoke including proximal and distal portions releasably and rotatably connected to one another via a first control wire, a distal end of the distal portion being connected to proximal ends of the clip arms. A second control wire extends from the handle assembly and is coupled to a proximal end of the second portion to move the clip assembly between open and closed configurations.

BRIEF DESCRIPTION OF THE DRAWINGS

FIG. 1A shows a detail view of an exemplary clip assembly of the clipping device;

FIG. 9 is a cross sectional side view of a distal end of a clipping device according to an embodiment of the present invention;

FIG. 10 is a cross sectional top view of a distal end of the clipping device shown in FIG. 9;

FIG. 16 is a top view of the distal end of a clipping device according to an embodiment of the present invention;

FIG. 17 is a side view of the distal end shown in FIG. 16;

FIG. 19 is a side view of the clip arm shown in FIG. 18;

FIG. 20 is a top view of the clip arm shown in FIG. 18;

FIG. 25 is a side view of a tension member according to an embodiment of the present invention;

FIG. 26 is a top view of the tension member shown in FIG. 25;

DETAILED DESCRIPTION

Hemostatic clips are used routinely to stop bleeding from openings created during surgery as well as wounds resulting from other trauma to tissues. In the simplest form, these clips grasp the tissue surrounding a wound and bring the wound's edges together, to allow the natural scarring process to heal the wound. In endoscopic hemostatic clips are used to stop internal bleeding due resulting from surgical procedures and/or tissue damage from disease, etc. Specialized endoscopic hemostatic clipping devices are used to bring the clips to the desired location within a patient's body and to position and deploy the clip at the appropriate place on the tissue. The clipping device is then withdrawn, leaving the clip within the patient.

Endoscopic hemostatic clipping devices are designed to reach affected tissues deep within a patient's body, such as within the GI tract, the pulmonary system, the vascular system or within other lumens and ducts. During the procedures to treat those areas, an endoscope is generally used to provide access to and visualization of the tissue which is to be treated. The clipping device may, for example, be introduced through a working lumen of the endoscope. The design and construction of such a "through the scope" endoscopic hemostatic clipping device presents several challenges. The endoscopic clipping device has to be sufficiently small to fit in the lumen of an endoscope and, at the same time, must be designed to provide for the positive placement and actuation of the hemostatic clip. Feedback to the operator is preferably also provided so that the operator will not be confused as to whether the hemostatic clip has been properly locked in place on the tissue and released from the device before the device itself is withdrawn through the endoscope.

Figure 1:
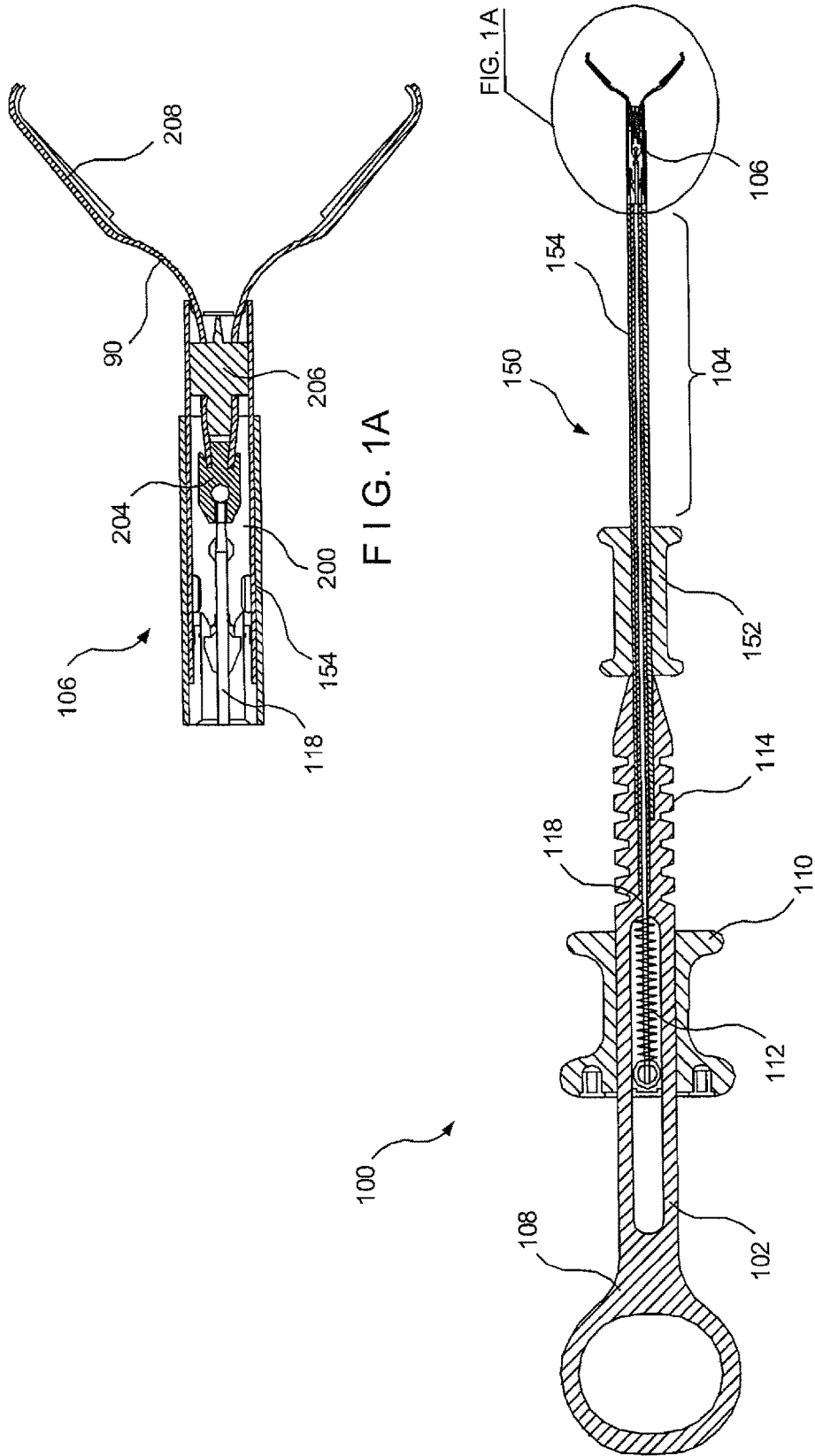
FIG. 1 is a schematic side view of a clipping device according to an exemplary embodiment of the present invention.

FIG. 1 shows a side elevation view of a through the scope hemostatic clipping device according to an exemplary embodiment of the present invention. This device is a hand operated tool that is used to insert a hemostatic clip through an endoscope lumen, position the clip over a wound, clamp it and deploy it over the affected tissue. The tool is further designed to release the hemostatic clip once it has been clamped in place, and to be withdrawn through the endoscope. To more clearly explain the operation and construction of the exemplary device, it may be divided into three principal components. As shown in FIG. 1, the hemostatic clipping device 100 comprises a handle assembly 102, a shaft section 104, and a clip assembly 106. A detailed view of the clip assembly 106 is shown in FIG. 1A.

Handle assembly 102 forms the component that supplies a mechanical actuation force to deploy and clamp the clip. In this embodiment, the device is hand operated (i.e., the user's hands provide the force required to carry out all the functions related to the hemostatic clip). The handle assembly 102 may be constructed in a manner similar to conventional handle assemblies of the type generally employed in endoscopic biopsy devices or in similar applications. The handle assembly 102 allows the user to move a control wire 118 or other force transmission member, which extends through the shaft section 104 to the clip assembly 106 at a distal end of the device 100. The handle assembly 102 comprises a handle body 108 which can be grasped by the user to stabilize the device and apply a force to it. A sliding spool 110 is connected to control wire 118, so that the user can easily pull or push said wire 118 as desired.

Figure 2:
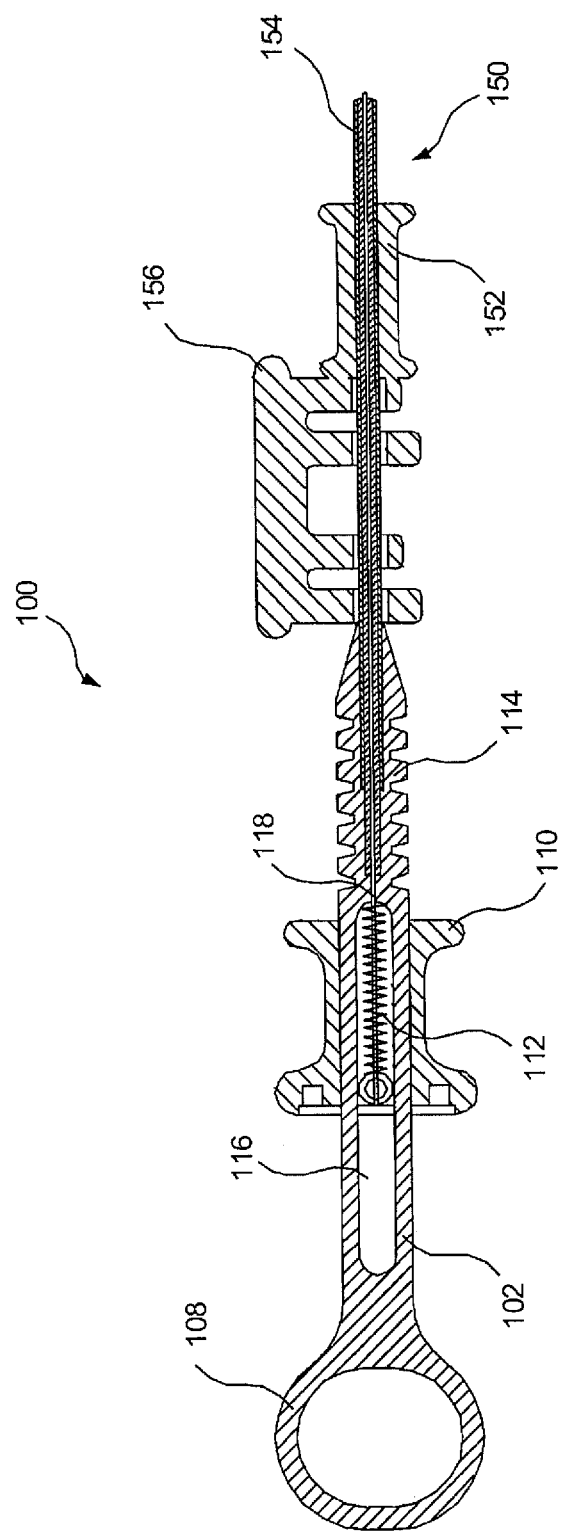
FIG. 2 is a schematic side view of the embodiment shown in FIG. 1, with a outer sheath.

As shown in FIGS. 1 and 2, a sliding spool 110 is mounted on the handle body 108 so that it can slide along a slot 116, which maintains its position within the handle assembly 102. Because the sliding spool 110 is connected to the control wire 118, the user may manipulate the control wire 118 by grasping the handle body 108 and moving the sliding spool 110 along the slot 116. A return spring 112 may be provided within the handle body 108 to bias the sliding spool 110, and thus the control wire 118 toward a desired position. In the present embodiment, the sliding spool 110 is biased to the proximal position. The handle assembly 102 may also include a connection portion 114, which receives the control wire 118 and attaches the shaft section 104 to the handle assembly 102.

Figure 4:
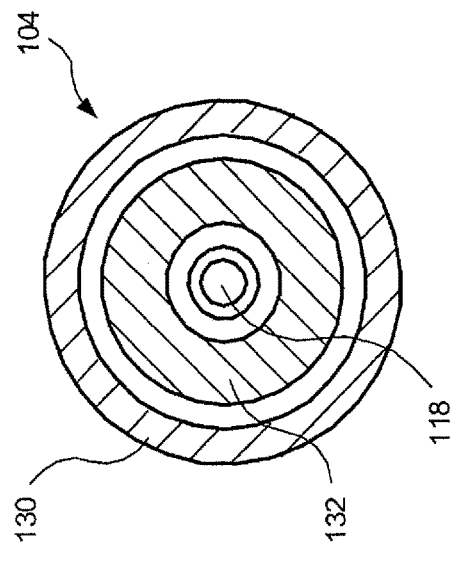
FIG. 4 is a cross sectional view of the shaft section shown in FIG. 3.
Figure 3:
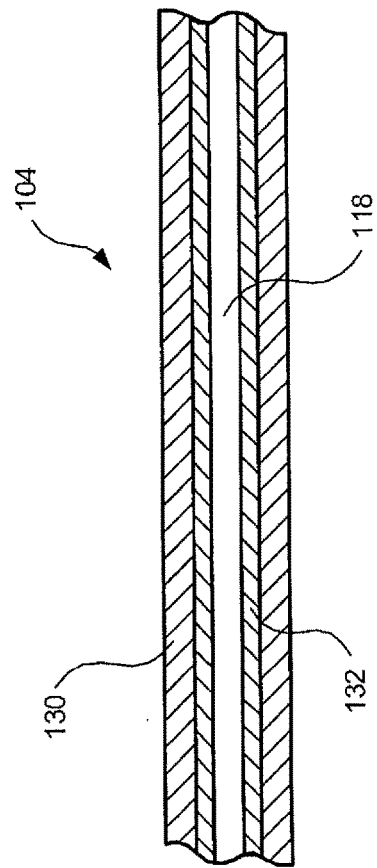
FIG. 3 is a cut away side view of the shaft section according to an embodiment of the present invention.

The shaft section 104 mechanically connects the handle assembly 102 to the clip assembly 106 and, together with the clip assembly 106, is designed to be inserted into a lumen of an endoscope. As shown in FIGS. 3 and 4, the shaft section 104 comprises an outer flexible coil 130 which is designed to transmit a torque from the proximal end to the distal end of the device 100 and to provide structural strength to the shaft section 104. The coil 130 may be a conventional coil used in biopsy devices and may, for example, comprise a single, coiled wire. The coiled wire may have a round, square or a rectangular cross section, and may be made of a biocompatible material such as, for example, stainless steel. Additional protective and low friction outer layers may be included on the shaft section 104, according to known methods of construction.

Figure 5:
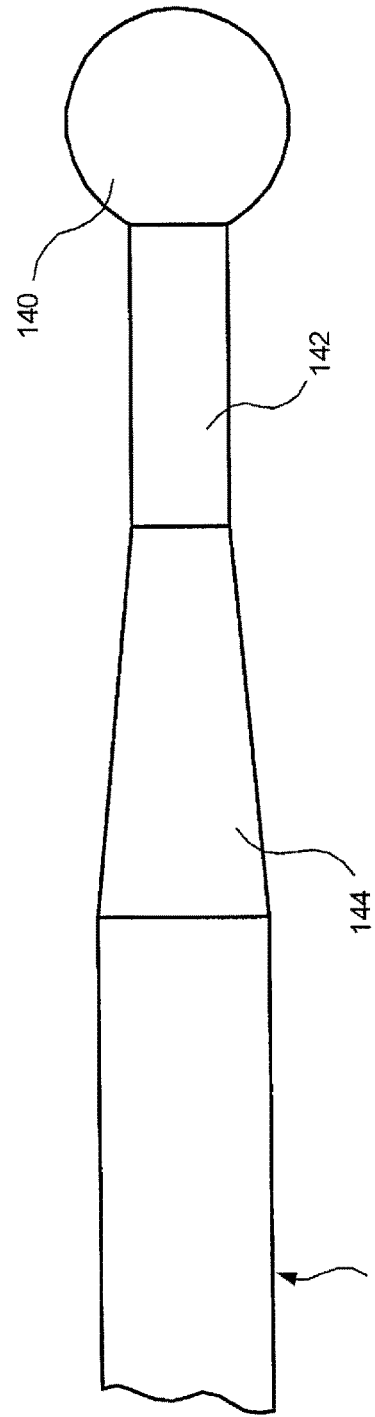
FIG. 5 is a detail view of the distal end of the control wire according to an embodiment of the present invention.

The control wire 118 transmits mechanical force applied to the handle 102 to the clip assembly 106. The control wire 118 has a proximal end which is attached to a movable part of the handle 102, such as the sliding spool 110, using known methods. Stainless steel or other high yield biocompatible materials may be used to manufacture the control wire 118, so that the structural integrity of the assembly is maintained. It is also important to prevent stretching of the control wire 118 when under tension since, if the wire stretches, the handle 102 will have to travel a greater distance to carry out a desired operation. As shown in FIG. 5, the distal end of the control wire 118 ends in a ball 140 which is used to connect the control wire 118 to the appropriate elements of the clip assembly 106, as will be described below. In this embodiment, the diameter of the control wire 118 is substantially constant from a proximal end thereof to a proximal end of a distal tapered section 144. The ball 140 may have a diameter which is greater than the diameter of the control wire 118, to facilitate attachment to a yoke 204. The control wire 118 may extend the length of the device 100, from the yoke 204 to the sliding spool 110, and slides longitudinally through the device 100. It may be made, for example, of stainless steel or other biocompatible metal.

The control wire 118 may also include a reduced diameter section 142 designed to fail when a predetermined tension is applied thereto through the handle assembly 102. The tapered section 144 may be used to transition between the main body of the control wire 118 and the reduced diameter section 142, without steps or other discontinuities which may concentrate stress and make the fracture point more unpredictable. As will be described in greater detail below, one purpose of the reduced diameter section 142 is to facilitate the release of a hemostatic clip from the hemostatic clipping device 100 once the clip has been properly deployed. It will be apparent to those of skill in the art that the location of the reduced diameter section 142 the along control wire 118 may be varied to take into account specific requirements of the device 100.

An inner sheath 132 may be used in the construction of the shaft section 104, as shown in FIGS. 3 and 4. The inner sheath 132 provides a low friction bearing surface disposed between the outer diameter of the control wire 118, and the inner diameter of the shaft section 104. The inner sheath 132 may be formed of a low friction material such as, for example, Teflon™, HDPE or Polypropylene. In one exemplary embodiment, the inner sheath 132 is slidable within the shaft section 104, and the control wire 118 is slidable within the inner sheath 132 forming a low friction system of multiple bearing surfaces. To further reduce friction, a bio-compatible lubricant may be applied to the inner and outer surfaces of the inner sheath 132, along the length of the shaft section 104. For example, silicone lubricants may be used for this purpose.

A slidable over-sheath 150 may be included in the design of the shaft section 104, as shown in FIGS. 1 and 2. The over-sheath 150 is designed to protect the inner lumen of the endoscope from the metal clip assembly 106 and from the metal coil 130 while the hemostatic clipping device 100 passes through the endoscope's lumen. After the clipping device 100 and, more specifically, after the clip assembly 106 has passed through the endoscope, the over-sheath 150 may be withdrawn to expose the distal portion of the clipping device 100. The over-sheath 150 may be formed, for example, as a single lumen plastic extrusion element slidable over the distal portions of the clipping device 100 to selectively cover and uncover the clip assembly 106. In one embodiment, the over-sheath 150 is formed of a low friction polymer such as, for example, Teflon™, HDPE, Polypropylene, or similar materials.

The over-sheath 150 may include a grip portion 152 and an elongated body 154. The grip portion 152 is designed as a handle making it easier for the user to slide the over-sheath 150 over the shaft of the clipping device 100. In one exemplary embodiment, the grip portion 152 is made of a rubber-like material to provide a good gripping surface for the user. For example, an injection moldable polymer such as TPE may be used to construct the grip portion 152. The elongated body 154 may be formed as a substantially cylindrical shell surrounding the shaft of the clipping device 100. The elongated body 154 may be attached to the grip portion 152 using conventional methods as would be understood by those skilled in the art.

Figure 6:
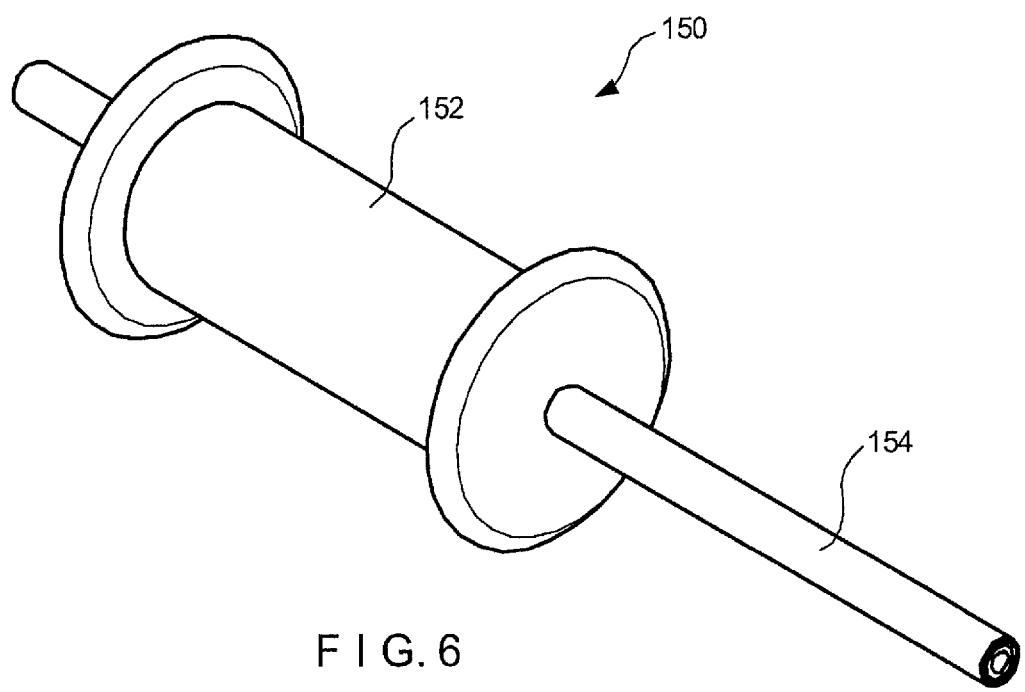
FIG. 6 is a perspective view of an outer sheath according to an embodiment of the present invention.
Figure 7:
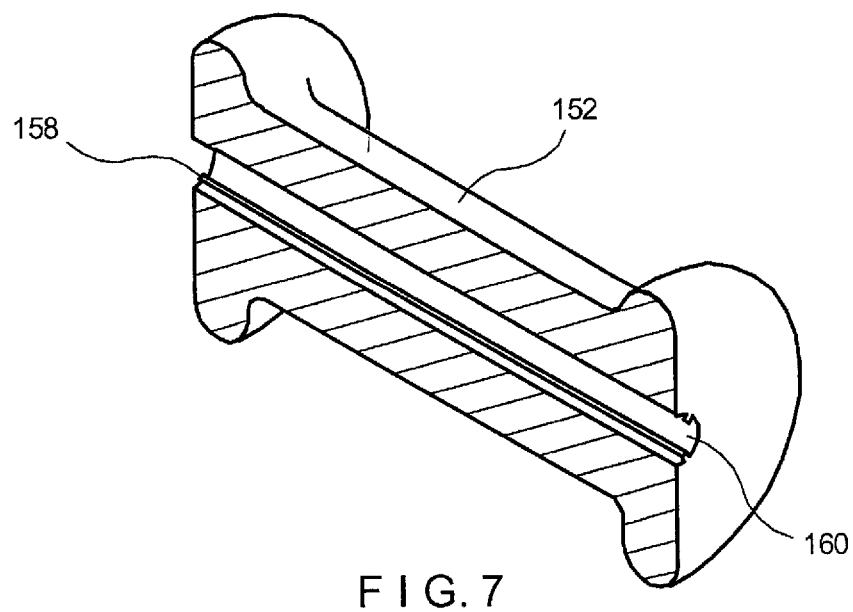
FIG. 7 is an cross sectional exploded view of the handle of the outer sheath shown in FIG. 6.

As shown in FIGS. 6 and 7, an exemplary grip portion 152 comprises a central hollow channel 160 that may be used to receive the shaft of the clipping device 100. The central hollow channel 160 is aligned with the elongated body 154 to provide a continuous channel containing the shaft of the clipping device 100. The material of the grip portion 152 may have a high coefficient of friction, so that an interference fit is possible between the central hollow channel 160 and the shaft of the clipping device 100 without the use of adhesives or mechanical fastening devices. In one embodiment, friction bosses 158 may be provided on an inner diameter of the hollow channel 160 to provide additional friction between the shaft of the clipping device 100 and the over-sheath 150 assembly. The friction bosses 158 may be formed, for example, as protrusions extending from the inner diameter of the over-sheath 150 and may have a variety of stubby or elongated shapes. The amount of friction between these two components may be balanced so that no unwanted relative movement takes place while, at the same time, making it relatively easy for the user to slide the over-sheath 150 proximally and distally when necessary.

Figure 8:
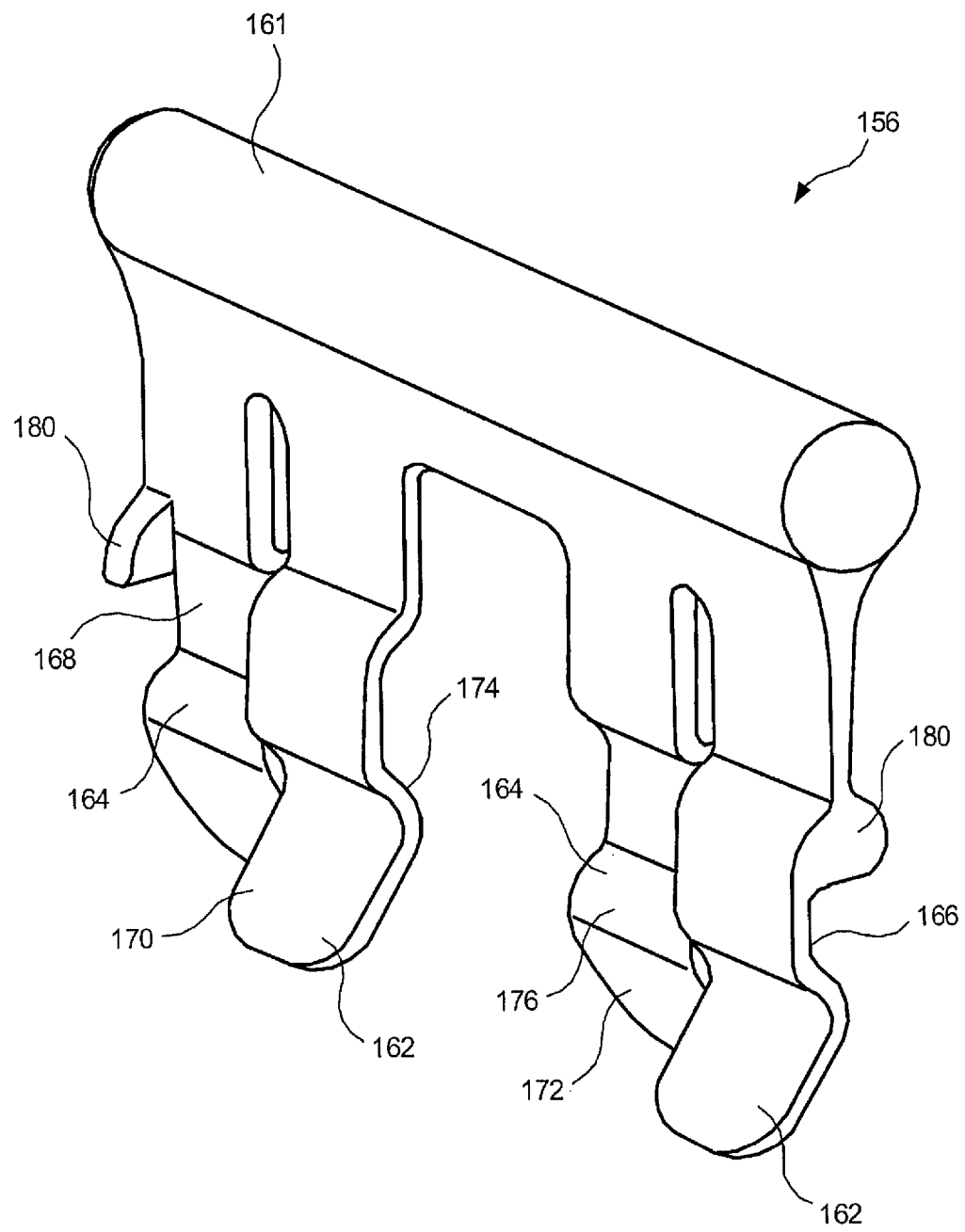
FIG. 8 is a perspective view of an outer sheath lock according to an embodiment of the present invention.

A sheath stop 156 may be provided for the clipping device 100 to prevent the over-sheath 150 from sliding away from the distal end while the clipping device 100 is inserted in the endoscope. As shown in the exemplary embodiment of FIGS. 2 and 8, the sheath stop 156 physically blocks the grip portion 152 from sliding proximally to prevent the oversheath 150 from being withdrawn and exposing the clip assembly 106. The sheath stop 156 is designed to easily snap in place near the proximal end of the shaft section 104 where it can be reached and manipulated by the operator during the surgical procedure. Once the clip assembly 106 has been inserted in the endoscope and has reached the desired location in the patient's body, the sheath stop 156 may be removed from the shaft section 104 so that the user can move the grip portion 152 proximally to uncover the clip assembly 106.

The connection between the sheath stop 156 and the shaft section 104 may include, for example, pairs of opposing fingers 162, 164 that are designed to snap over the shaft section 104. The fingers 162, 164 cooperate to securely and releasably hold the body of the shaft section 104 therebetween. The fingers 162, 164 respectively comprise guide portions 170, 172; shaft channel portions 166, 168; and blocking portions 174, 176. Insertion of the sheath stop 156 on the elongated body 154 is accomplished by pressing the body of the shaft section 104 between the guide portions 170, 172, to spread the fingers 162, 164 and allow further insertion of the shaft 104 between the fingers 162, 164. The guide portions 170, 172 and the blocking portions 174, 176 are shaped so that insertion of the shaft section 104 towards the channel portions 166, 168 requires less effort than moving the shaft section 104 in the opposite direction.

Once shaft section 104 has been placed within the channel portions 166, 168, the fingers 162, 164 snap back to their non-spread position and retain the shaft section 104 in place therebetween. The shaft section 104 is removed by pulling the sheath stop 156 away from the shaft section 104. Due to the shape of the blocking portions 174, 176, removing the shaft section 104 requires the application of more force than does insertion thereinto. Stops 180 may also be provided on the sheath stop 156 to limit the movement of the shaft section 104 towards the grasping portion 161 to prevent damage to the device that may be caused by excessive spreading of the fingers 162, 164. The sheath stop 156 may be formed of a resilient material, such as a polymer, and may be manufactured by injection molding.

Figure 11:
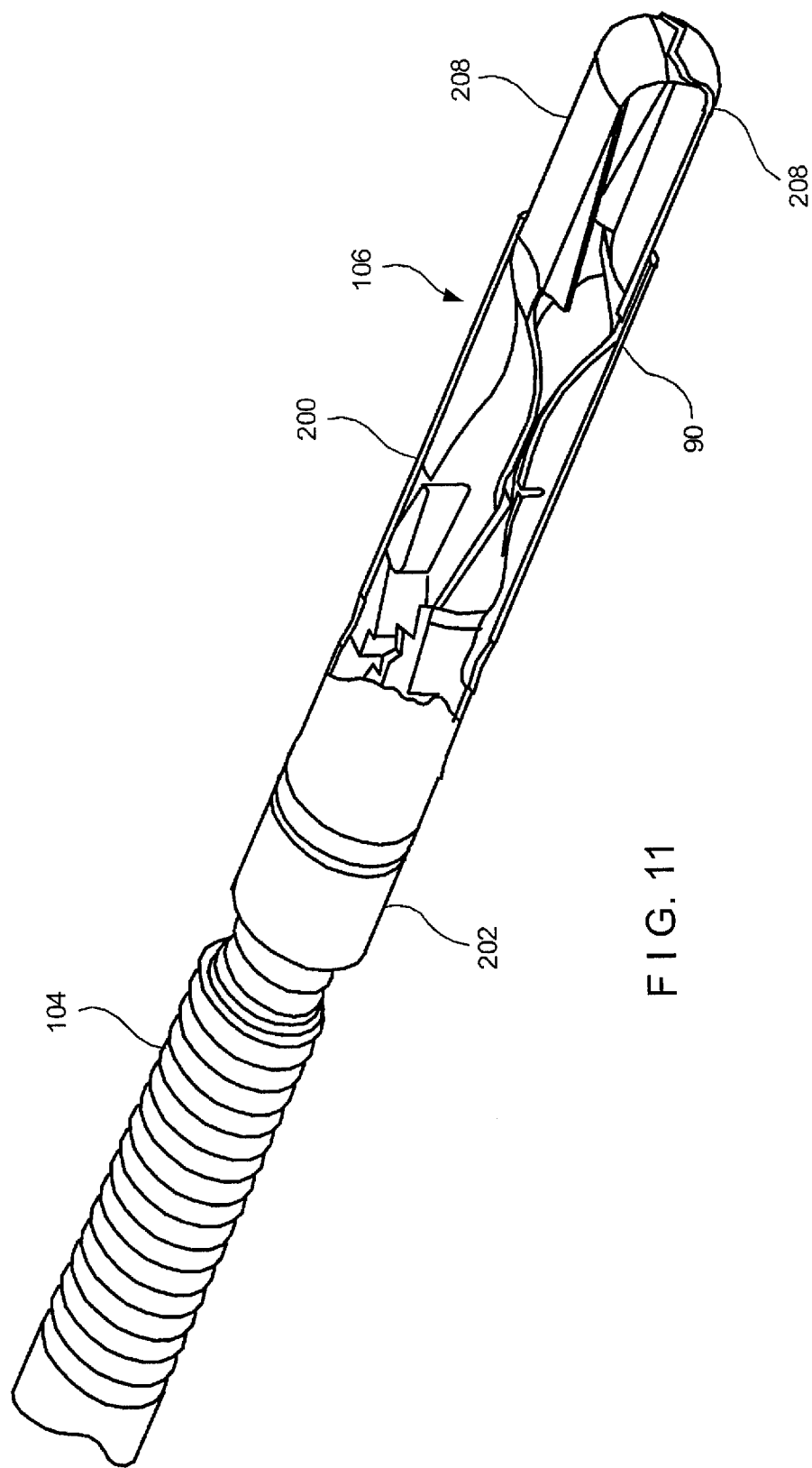
FIG. 11 is a perspective view of the distal end of the clipping device shown in FIG. 9.

The clip assembly 106 is disposed at the distal end of the clipping device 100, and contains the mechanism that converts the proximal and distal movement of the control wire 118 into the actions necessary to deploy and release a hemostatic clip 90. FIGS. 9, 10 and 11 show, respectively, side, top and perspective views of the distal end of the clipping device 100, including the clip assembly 106 having clips in the folded configuration. This configuration is used, for example, to ship the clipping device 100 and to insert the clipping device 100 through the lumen of an endoscope. Some of the components of the clip assembly 106 include a capsule 200 which provides a structural shell for the clip assembly 106, the clip arms 208 which move between open and closed positions, a bushing 202 attached to the distal end of the control wire 118, and a yoke 204 adapted to connect the capsule 200 to the control wire 118.

As depicted, the proximal end of the capsule 200 slides over the distal end of the bushing 202. A locking arrangement between these two components is provided by capsule tabs 212, which are designed to lock into the bushing 202 so that mechanical integrity is temporarily maintained between the capsule 200 and the bushing 202. Within the capsule 200 are contained a yoke 204 and a tension member 206 which transmit forces applied by the control wire 118 to the clip arms 208. The ball 140 formed at the distal end of the control wire 118 is mated to a receiving socket 210 formed at the proximal end of the yoke 204. A male C-section 214 extending from the tension member 206 is received in a corresponding female C-section 216 formed in the yoke 204, so that the two components are releasably connected to one another, as will be described below. The clip arms 208 in the closed configuration have a radius section 300 which is partially contained within the capsule 200 to prevent opening of the arms. Each of the clip arms 208 goes over the tension member 206 and has a proximal end 222 which slips under a yoke overhang 254, to further control movement of the arms 208.

Figure 12:
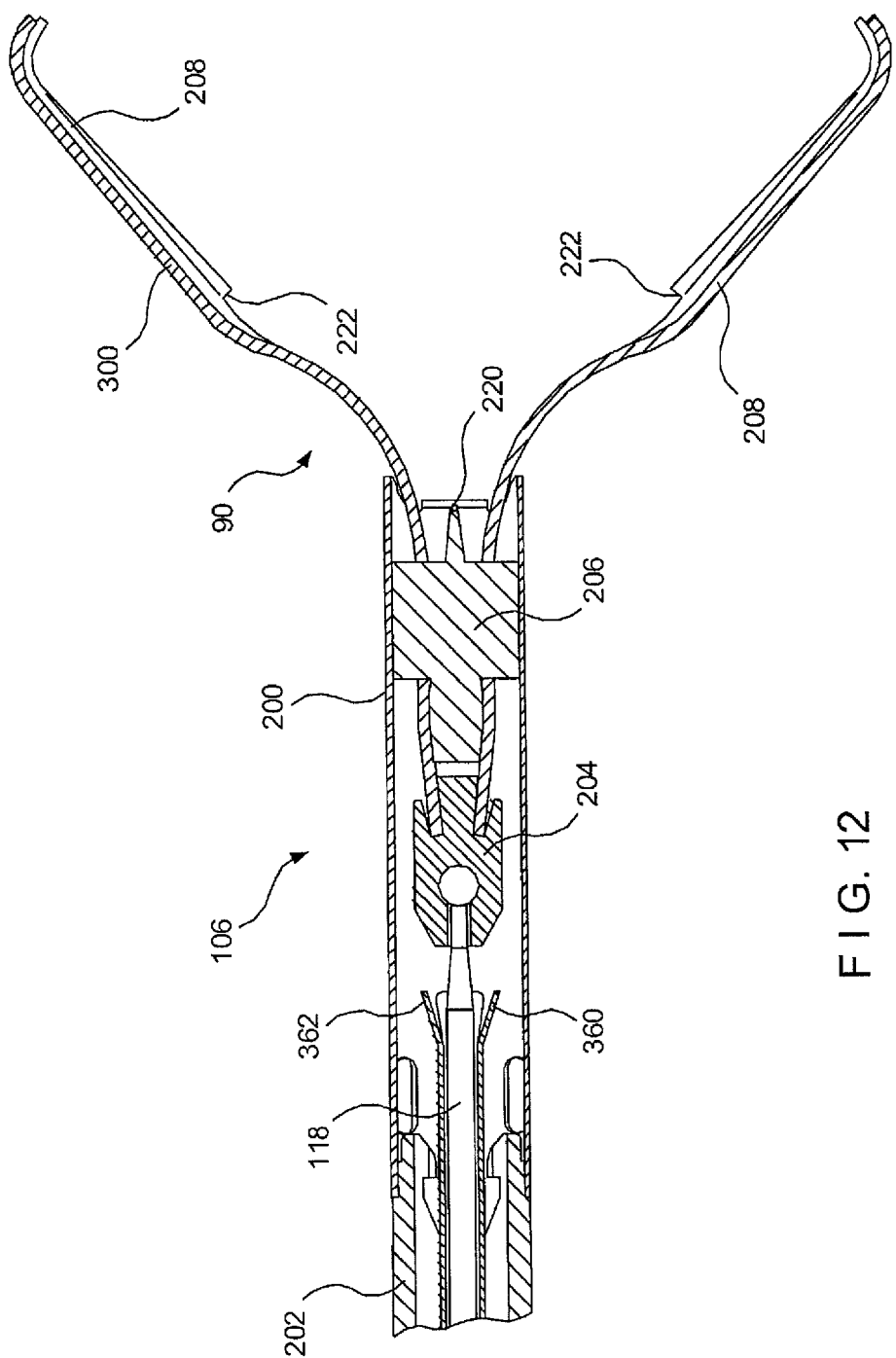
FIG. 12 is a top view of the clip arms according to an embodiment of the present invention.
Figure 13:
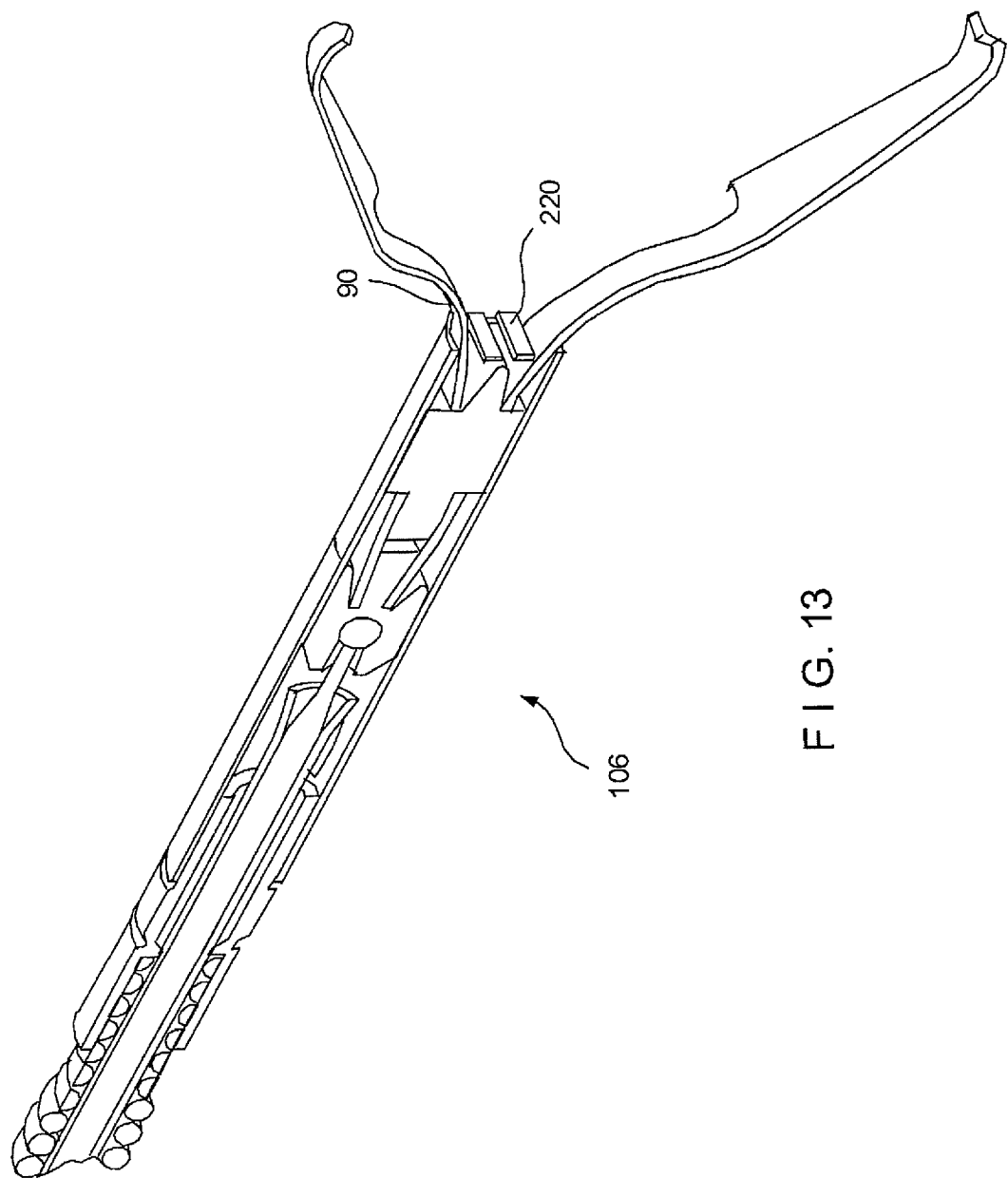
FIG. 13 is a perspective view of the clip arms shown in FIG. 12, according to an embodiment of the present invention.
Figure 14:
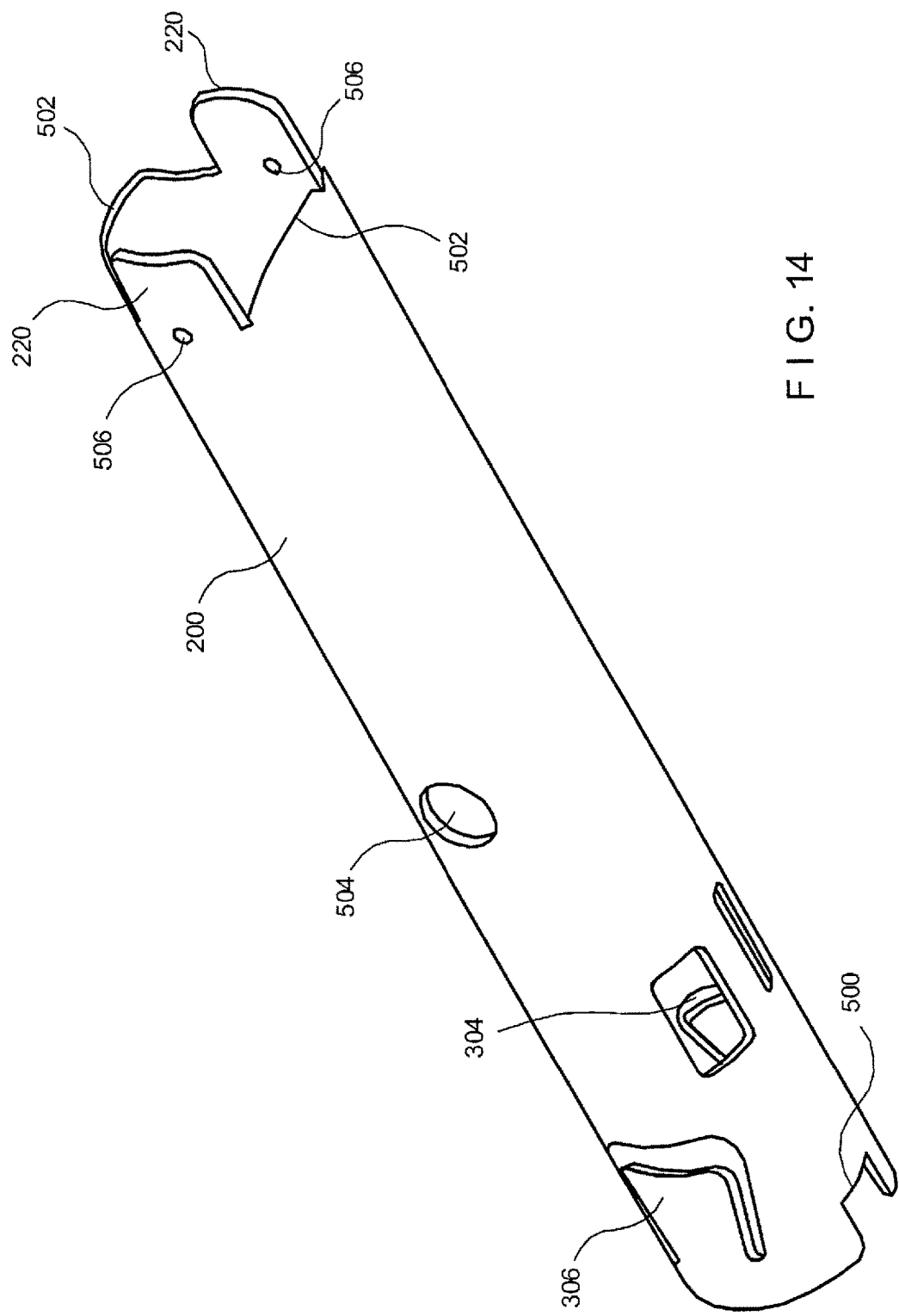
FIG. 14 is a perspective view of a capsule according to an embodiment of the present invention.
Figure 15:
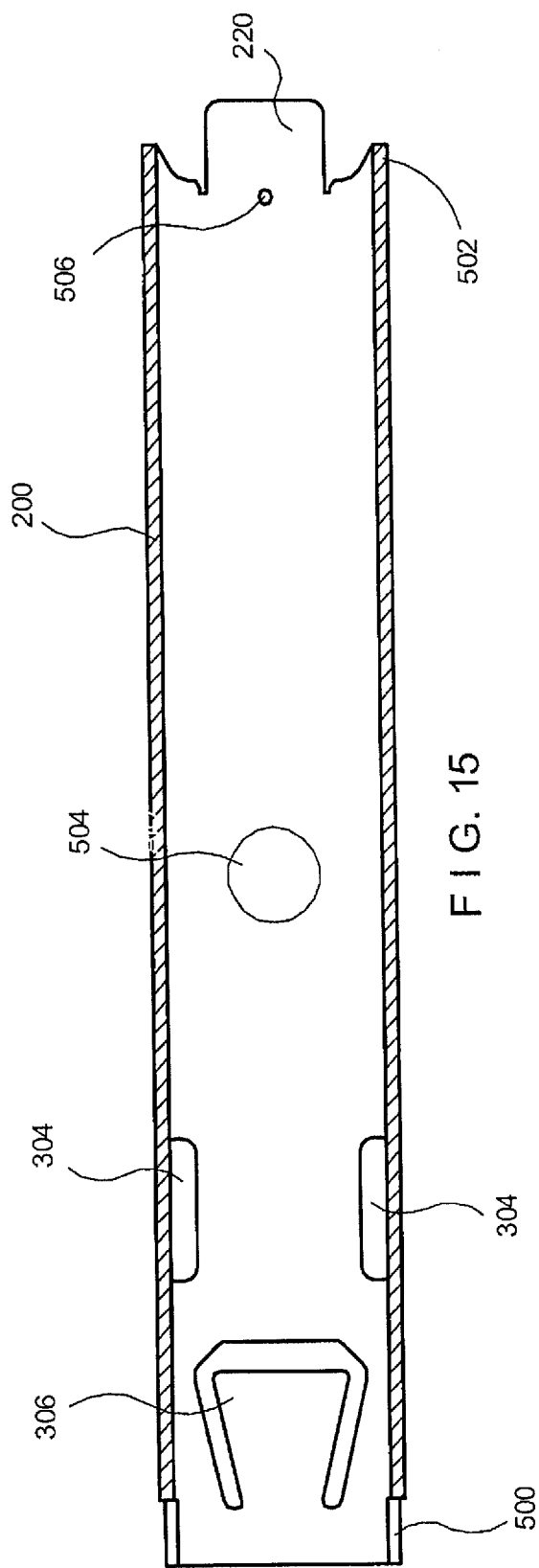
FIG. 15 is a cross sectional side view of the of the capsule shown in FIG. 14.

FIGS. 12 and 13 show a top and a perspective view of the clip assembly 106 in an open configuration with the clip arms 208 in a fully open position. The open configuration is obtained when the sliding spool 110 shown in FIG. 1 is moved distally so that the ball 140 of the control wire 118 pushes the assembly containing the yoke 204 and the tension member 206 forward, sliding within the capsule 200. As will be described below, the distal ends of the clip arms 208 are biased toward the open position and revert to this position whenever they are not constrained by the capsule 200. In the exemplary embodiment, a maximum opening of the clip arms 208 occurs when the clip arms 208 ride over the folded distal folding tabs 220 which extend from the distal end of the capsule 200, as shown in FIGS. 14 and 15. In this embodiment, the tabs 220 provide a cam surface, and the clip arms 208 act as cam followers, being deflected by the tabs 220. In addition, the folding tabs 220 may also provide a distal stop for the tension member 206, to retain it within the capsule 200. Thus, by moving the sliding spool 110 distally, the user opens the clip arms 208 to prepare to grasp tissue therebetween.

When the sliding spool 110 is moved proximally by the user, the assembly within the capsule 200 also moves proximally and the clip arms 208 are withdrawn within the capsule 200. As the clip arms 208 move proximally within the capsule 200, clip stop shoulders (CSS) 222 contact a distal portion of the capsule 200, for example, the folded tabs 220. This interaction of the CSS 222 with the capsule 200 provides to the user a first tactile feedback in the form of increased resistance to movement of the sliding spool 110. This feedback gives to the operator a positive indication that further movement of the handle control will cause the hemostatic clip 90 to be deployed from the clip assembly 106. The operator may then decide whether the current position of the clip 90 is acceptable or not. If the position is acceptable, the operator can deploy the clip 90 by continuing to move the sliding spool 110 with increased proximal pressure to cause the clip arms 208 to close on the tissue. If not, the operator can move the sliding spool 110 distally to re-open the clip arms 208 and extend them out of the capsule 200, reposition the clip 90, and repeat the above steps to close the clip 90 at a more appropriate location.

When the user determines that the clipping device 100 is positioned correctly, the proximal pressure on the sliding spool 110 may be increased to continue deployment of the hemostatic clip 90 from the clip assembly 106. FIGS. 16 and 17 show respectively a top and side view of the clipping device 100 in this condition. As the proximal tension on sliding spool 110 is increased, the control cable 118 pulls the yoke 204 proximally, away from the tension member 206. The tension member 206 is firmly attached to the clip arms 208 which are prevented from moving proximally by the interaction of the CSS 222 with the folded tabs 220. If sufficient pulling force is applied to the yoke 204, the male C section 214 of the tension member 206 yields and loses integrity with the female C section 216 of the yoke 204. This can occur because, in the exemplary embodiment, the tension member 206 is formed of a material with a lower yield strength than the material of the yoke 204.

The force required to break the tension member 206 away from the yoke 204 may be tailored to achieve a desired feedback that can be perceived by the user. The minimum force required to break the tension member 206 free of the yoke 204 may be selected so that a tactile feedback is felt by the user, to prevent premature deployment of the hemostatic clip 90 while a maximum force may be selected so that other components of the linkage between the sliding spool 110 and the clip arms 208 do not fail before the male C section 214 and the female C section 216 disconnect from one another. In one exemplary embodiment, the tension force necessary to disconnect the two components may be in the range of approximately 4 lbf to about 12 lbf. This range may vary depending on the size of the device and the specific application. To obtain this force at the interface of the male and female C sections 214, 216 a larger force will be applied by the user at the sliding spool 110, since friction within the device may cause losses along the long flexible shaft.

Figure 18:
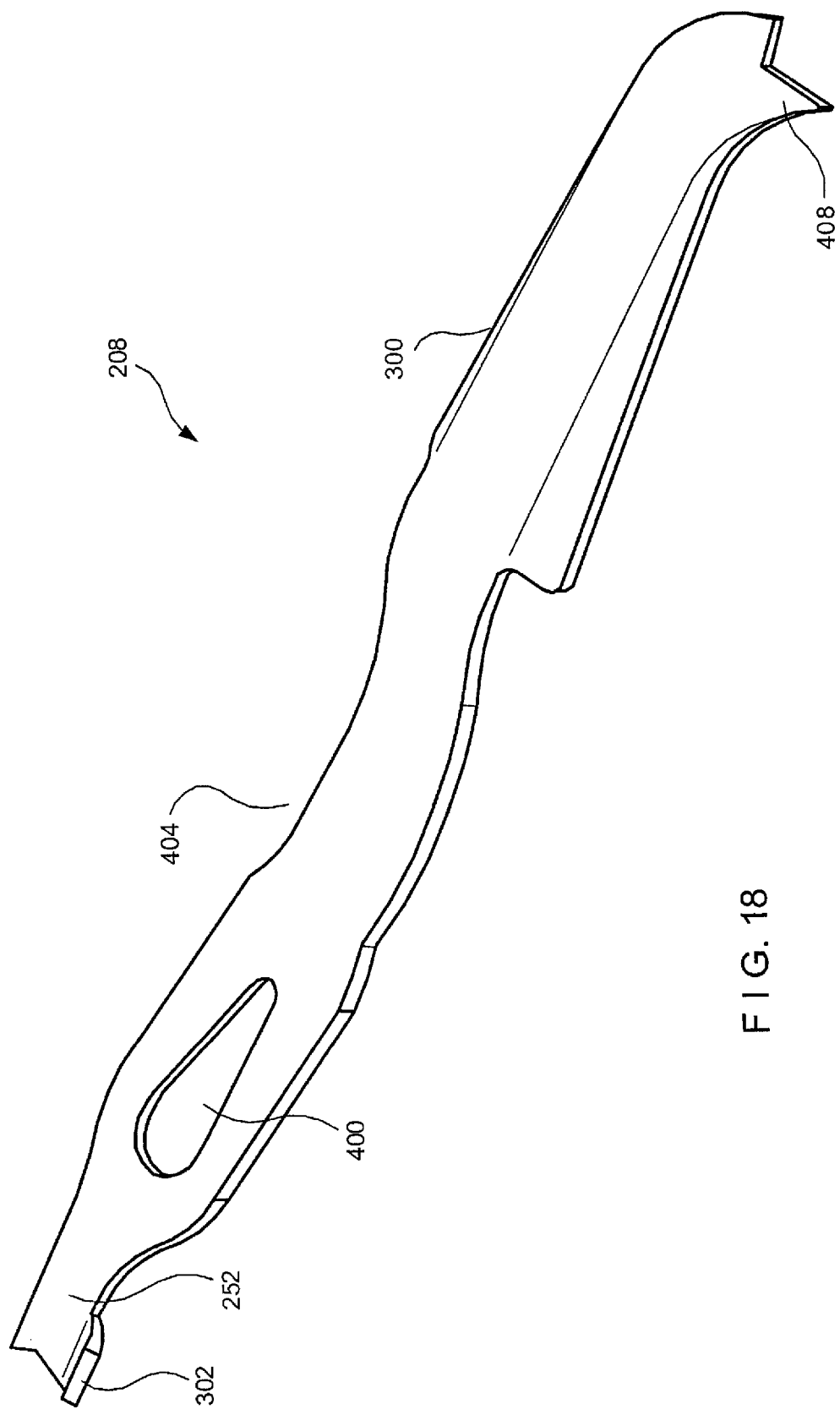
FIG. 18 is a perspective view of a clip arm according to an embodiment of the present invention.

When the male C section 214 of tension member 206 yields, several events take place within the device 100 nearly simultaneously. More specifically, the yoke 204 is no longer constrained from moving proximally by the CSS 222 abutting the capsule 200. Thus the yoke 204 travels proximally until coming to rest against a distal bushing shoulder 250. The tension member 206 is not affected by this movement since it is no longer connected to the yoke 204. The proximal ends 252 of the clip arms 208 are normally biased away from a center line of the device 100 and are no longer constrained by the yoke overhangs 254. Accordingly, the clip latches 302 are free to engage the latch windows 304 of the capsule 200, thus maintaining the integrity of the capsule-clip arms combination after deployment. Details of the capsule 200 are shown in FIGS. 14, 15 and details of the clip arms 208 are shown in FIGS. 18, 19 and 20.

Figure 21:
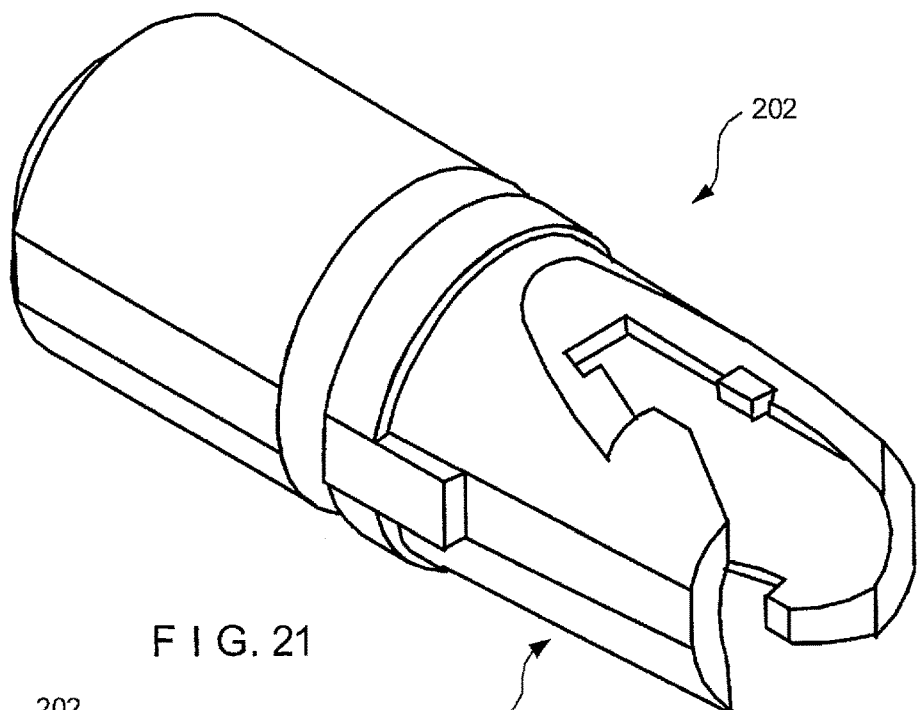
FIG. 21 is a perspective view of a bushing according to an embodiment of the present invention.

As the yoke 204 moves proximally to abut against the bushing 202, the capsule tabs 306 are bent away from the centerline of the capsule 200 by the cam surfaces of the yoke 204. As a result, the capsule tabs 306 are no longer engaged to the corresponding bushing undercuts 350, shown in the side and perspective views of the bushing 202 depicted in FIGS. 21, 22. Since the capsule 200 and the bushing 202 (which is securely connected to shaft section 104) are no longer connected, the clip assembly 106 is prevented from being released from the shaft section 104 only by its connection to the ball 140 of the control wire 118.

Figure 22:
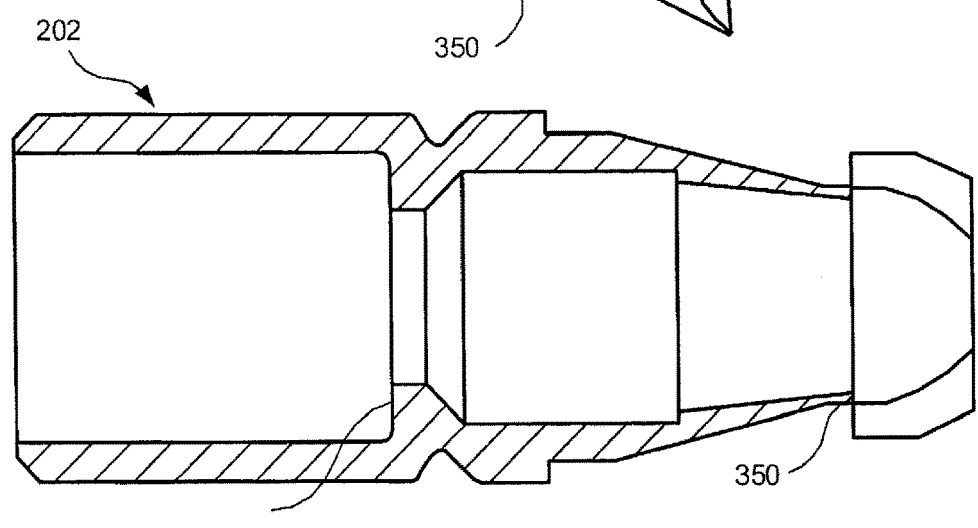
FIG. 22 is a cross sectional side view of the bushing shown in FIG. 21.
Figure 23:
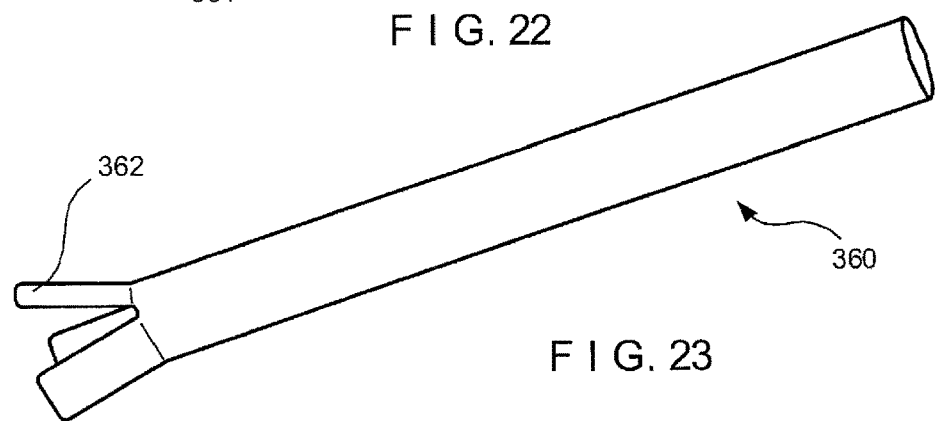
FIG. 23 is a perspective view of a wire stop according to an embodiment of the present invention.

A further result of moving the yoke 204 against the distal bushing shoulder 250 of the bushing 202 is that the distal end of the wire stop 360 (shown in FIGS. 12, 16) is placed near the proximal bushing shoulder 364 (shown in FIG. 22). The flared fingers 362 located at the distal end of the wire stop 360, better shown in FIG. 23, are compressed as they pass through the central ID of the bushing 202, but return to their normally biased open position (shown in FIG. 23) after passing past the proximal bushing shoulder 364. Further distal movement of the sliding spool 110 is thus prevented since that movement would engage the fingers 362 of the wire stop 360 with the proximal bushing shoulder 364. This feature prevents the clip assembly 106 from being pushed away from the bushing 202 before the ball 140 is separated from the control wire 118, as will be described below.

The wire stop 360 comprises a tube with a first slotted and flared end attached to the control wire 118 by conventional means. As shown in FIG. 23, the slots impart flexibility to the device so it can easily pass through the central lumen of the bushing 202. Flared fingers 362 are formed by the slots, and engage the proximal bushing shoulder 364. The wire stop 360 is made of a material that is biocompatible and that has enough resilience so that the fingers 362 re-open after passage through the bushing 202. For example, stainless steel may be used for this application.

One feature of the exemplary embodiment of the invention described above is that the user receives both tactile and auditory feedback as the clip assembly 106 is deployed and released. The separation of the tension member 206 from the yoke 204 produces a small clicking noise and a tactile feel that is perceptible while holding the handle assembly 102. The change in axial position of the sliding spool 110 is thus augmented by the changes in resistance to its movement and by the clicking sound and feel through the start and stop of the movement. As a result the user is always aware of the status of the clip assembly 106, and the inadvertent deployment of a hemostatic clip 90 in an incorrect location is made less likely. It will be apparent to those of skill in the art that the order of male and female connectors in the device may be reversed or changed without affecting the operation of the device.

Figure 24:
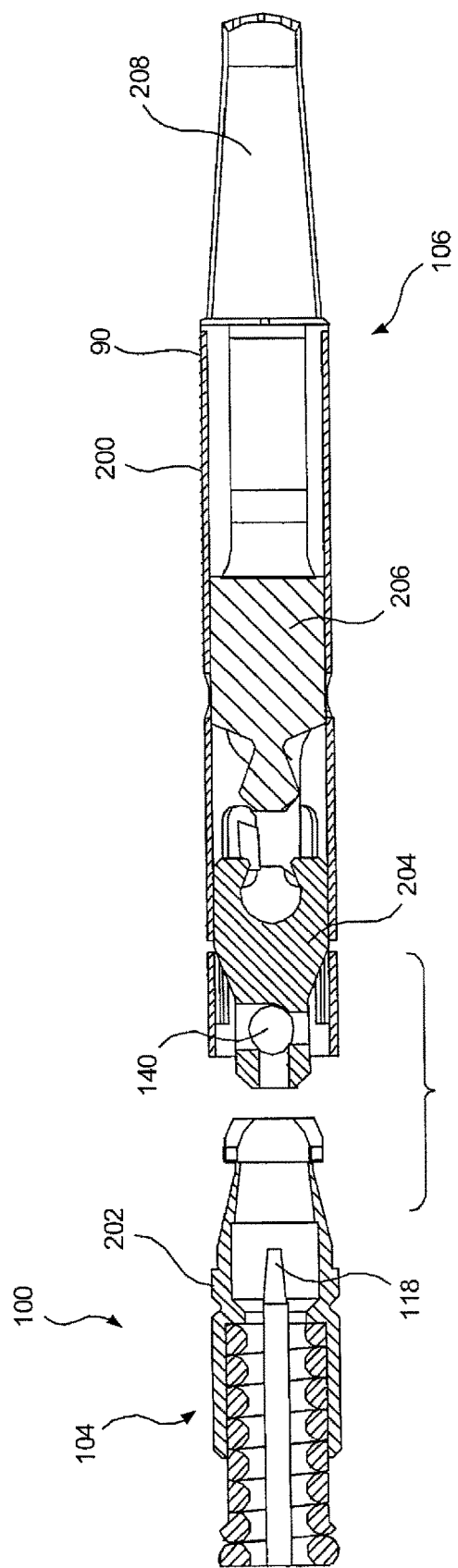
FIG. 24 is a schematic side view of a clip assembly detached from a bushing, according to an embodiment of the present invention.

It may be beneficial for the user to be certain that the clip assembly 106 has been deployed before the rest of the clipping device 100 is removed from the endoscope. Injury to the tissue being treated could result if the clipping device 100 is removed from the operative site when the hemostatic clip 90 is only partially deployed. Accordingly, a large tactile feedback may be incorporated, to augment the auditory and tactile feedback stemming from the separation of the yoke 204 from the tension member 206. FIG. 24 depicts the condition where the clip assembly 106 separates from the rest of the clipping device 100. According to the described embodiment, this second user feedback is obtained by designing the control wire 118 so that it will separate from the end ball 140 when a predetermined tension is applied to it. In other words, the ball 140 of the control wire 118 is mechanically programmed to yield and separate from the body of the control wire 118 when a pre-set tension is applied thereto. The size of the reduced diameter section 142 can be selected so that, when the user continues to move the sliding spool 110 proximally as the programmed yield tension is reached, the ball 140 detaches from the tapered section 144 and provides a large tactile feedback to the operator.

When the ball 140 detaches, the sliding spool 110 bottoms out at the proximal end of the handle 108, such that a full stroke of the handle assembly 102 is reached. The tension required to cause the reduced diameter section 142 to yield and release the ball 140 may vary over a range of values. However, for best results the force should be greater than the tension force required for the male C section member 214 to separate from the yoke 204. If this condition is not satisfied, a situation may occur where the clip assembly 106 is locked in place on the patient's tissue, but cannot be released from the clipping device 100. It will be apparent that this situation should be avoided. In one exemplary embodiment, the tension force required to separate the ball 140 from the body of the control wire 118 is in the range of between about 10 lbf and 20 lbf at the distal end of the control wire 118. As discussed above, losses along the elongated flexible shaft may require the user to apply a force substantially greater than this to the handle body 102.

Once the ball 140 has separated from the rest of the control wire 118, the user can pull the rest of the clipping device 100 from the endoscope. As this is done, the yoke 204 is retained within the capsule 200 by the spring and frictional forces of the capsule tabs 306. Prior to withdrawing the clipping device 100, the over-sheath 150 may be moved distally by the user over the entire remaining portions of the shaft section 104 to prevent damage to the endoscope as the clipping device 100 is withdrawn therethrough. The sheath stop 156 may also be placed on the shaft section 104 proximally of the over-sheath grip 152 to prevent inadvertent sliding of the over-sheath 150 from the distal end of the device 100.

A more detailed description of several components of the clipping device 100 follows. The clip arms 208 are shown in detail in FIGS. 18, 19 and 20; the tension member 206 is shown in side and top views in FIGS. 25, 26; while top and side views of the yoke 204 are shown respectively in FIGS. 27 and 28. the clip arms 208 may be formed of a biocompatible material such as Nitinol, Titanium or stainless steel. Maximum spring properties may be obtained by using materials such as 400 series stainless or 17-7 PH. As shown, a tear drop keyway 400 is formed in the clip arm 208 to mate with a corresponding tear drop key 402 formed on the tension member 206. This feature maintains the relative positions of these two components and of the yoke 204 substantially constant. The shape of the keyways 400 may be varied. For example, the keyway 400 may be oval or elliptical. Central portions of the clip arms 208 define a spring section 404. When the proximal ends 252 of the clip arms 208 are under the yoke overhangs 254, the clip arms 208 are allowed to pivot over the tension member 206, which in turn biases the distal ends 252 towards the open configuration when no longer restrained by the capsule 200. As a result, the proximal end 252 of each clip arm 208 springs upward and engages the latch windows 304 in the capsule 200.

The clip arms 208 also comprise a radius section 300 that adds strength to the clip and reduces system friction. The radius of the radius section 300 approximately matches the inner diameter of the capsule 200 and has a smooth profile to avoid scratching the inner surface of the capsule 200. A pre-load angle α is defined between the radius section 300 and the spring section 404. The pre-load angle α determines how much interference (pre-load) exists between the two opposing clip arms 208 at their distal ends when closed. The greater the pre-load angle α, the greater the engaging force that is applied by the clip arms 208. However, this condition also causes the greatest system friction when the hemostatic clip 90 is closed. The clip arms 208 also comprise interlocking teeth 408 disposed at their distal ends. In the exemplary embodiment, the teeth 408 are identical so that the arms may be interchangeable and will mesh smoothly with the set facing them. The teeth 408 are disposed at a nose angle β which may be between approximately 90 and 135 degrees, but in other applications may be greater or lesser than the described range.

The capsule 200 is shown in detail in FIGS. 14 and 15 and comprises alignment keyways 500 that are designed to mate with corresponding features on the bushing 202 to rotationally align the two components. The capsule tabs 306 may be bent towards the centerline of the capsule 200 to engage the bushing undercuts 350. The engagement maintains the integrity between the capsule assembly 200 and the rest of the clipping device 100 until the yoke is pulled into the distal bushing shoulder. the capsule overhangs 502 provide added clamping strength to the deployed clip arms 208. This is achieved by reducing the length of the portion of each clip arm 208 that is not supported by a portion of the capsule 200. This feature does not affect the amount of tissue that may be captured by the clip arms 208 since the capsule overhangs 502 extend on a plane substantially parallel to the plane of the clip arms 208.

Additional features of the capsule 200 include an assembly aid port which may be used to assist in aligning the components of the clip assembly 106. Bending aids 506 facilitate a smooth bend when the distal folding tabs 220 are bent inward, as described above. The bending aids 506, as shown, are holes aligned with the folding line of the tabs 220, but may also include a crease, a linear indentation, or other type of stress concentrator. The capsule 200 may be formed from any of a variety of biocompatible materials. For example, stainless steel, Titanium or Nitinol or any combination thereof may be used. High strength polymers like PEEK™ or Ultem™ may also be used to form the capsule 200, with a heat set treatment being used to adjust positionable elements.

FIGS. 25 and 26 depict additional details of the tension member 206. As shown, tear drop keys 402 are designed to engage the tear drop keyways 400 of the clip arms 208, as described above. Clip follower planes 508 are shaped to form a fulcrum which allows the clip arms 208 to rock between the open and closed configurations. The tension member 206 comprises a distal stop face 510 which abuts the distal folding tabs 220 of the capsule 200 to stop the distal motion of the capsule assembly 106. In general, all surfaces and edges of the tension member 206 that are in contact with the inner surfaces of the capsule 200 preferably have a radius substantially similar to an inner radius of the capsule 200 to provide a sliding fit therein. The tension member 206 may be formed of a biocompatible polymer, monomer or thermoset. The type of mechanism selected to release the tension member 206 from the yoke 204 may determine the type of material used since a release due to fracture of the male C section 214 requires a relatively brittle material while release due to yielding without fracture calls for a softer material.

Figure 27:
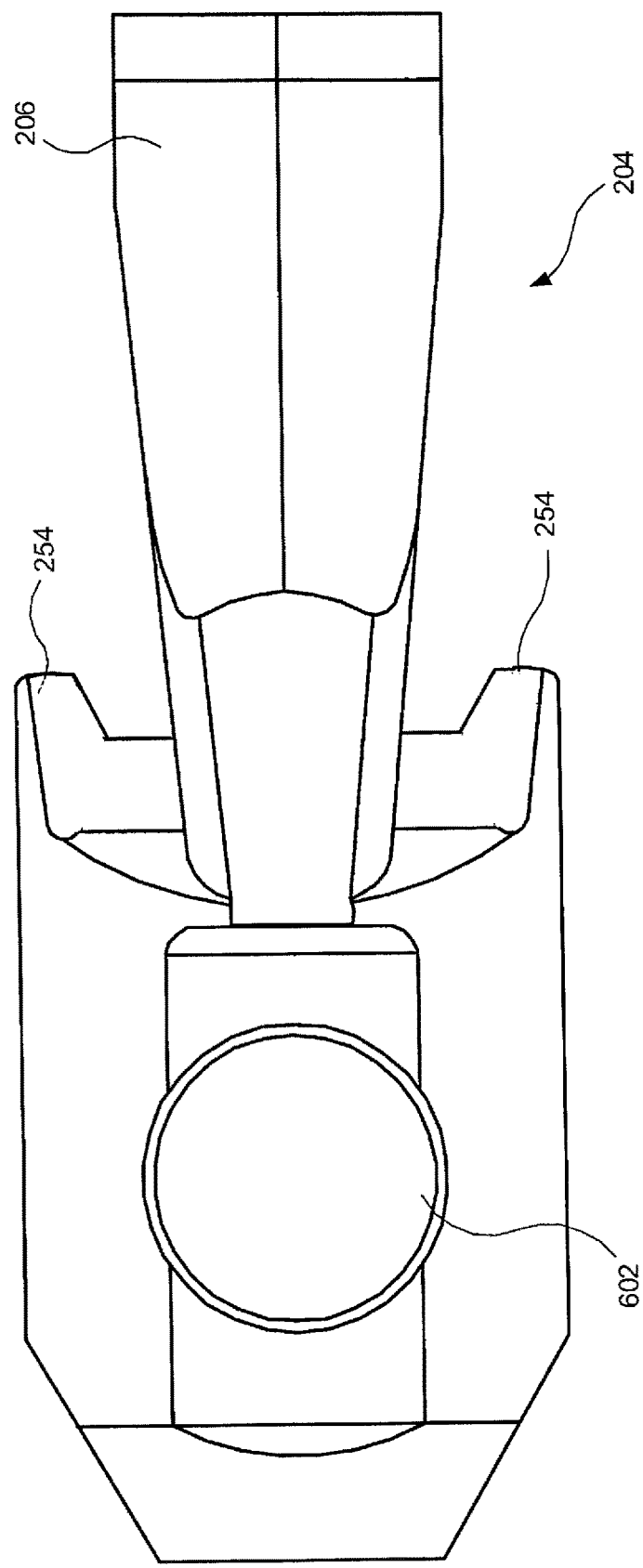
FIG. 27 is a top view of a yoke according to an embodiment of the present invention.
Figure 28:
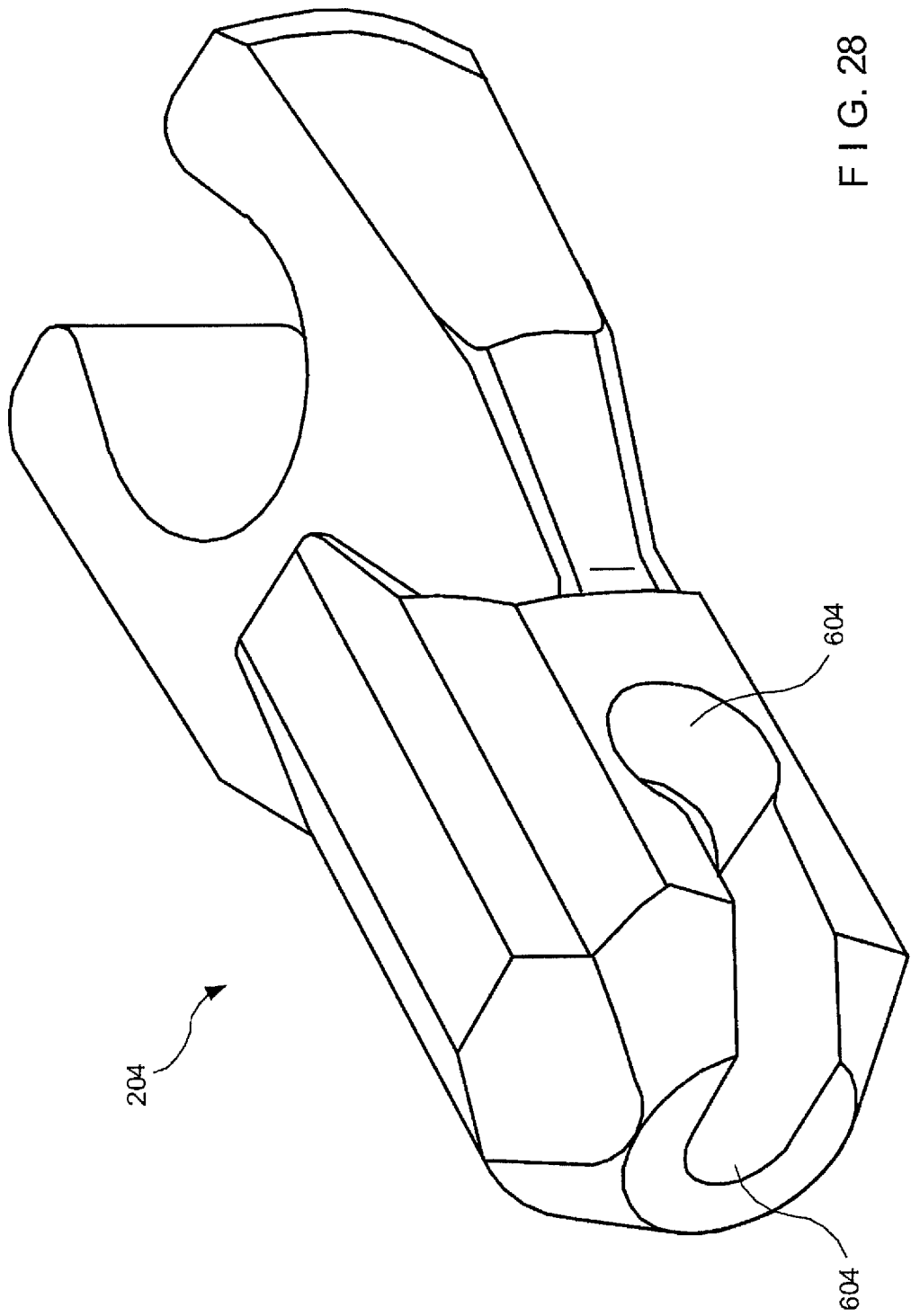
FIG. 28 is a perspective view of the yoke shown in FIG. 27.
Figure 29:
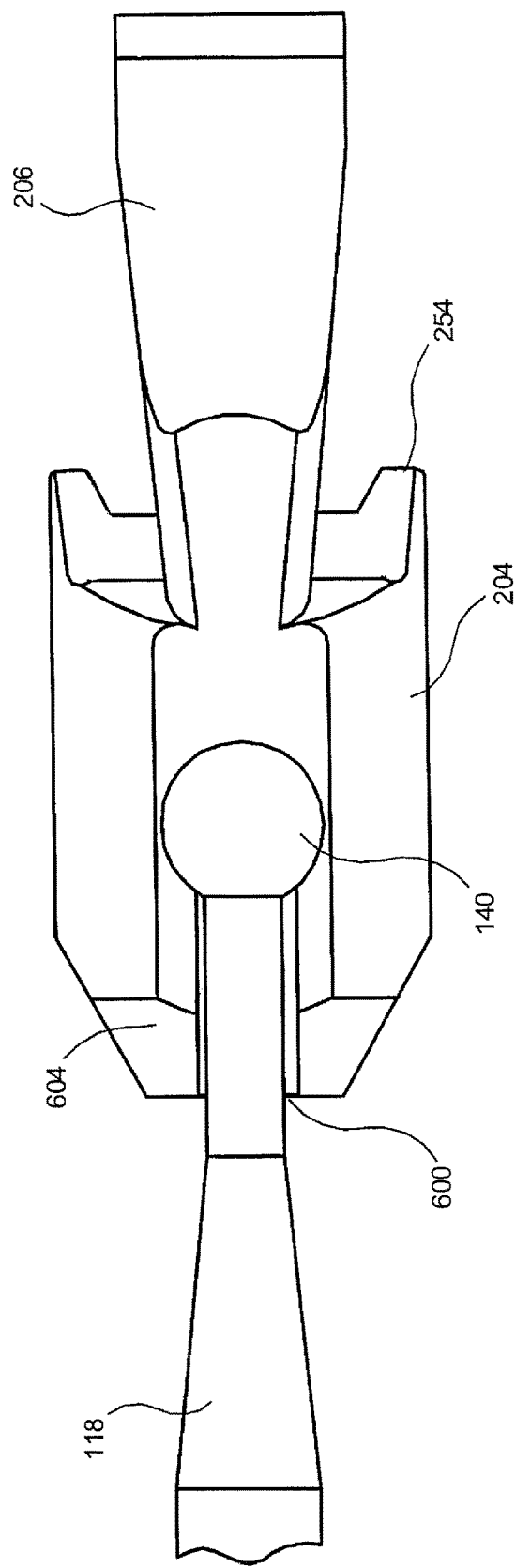
FIG. 29 is a top view of a yoke with a control wire according to an embodiment of the present invention.

Additional details of the yoke 204 are shown in FIGS. 27-29. When the control wire 118 is seated in the yoke 204, it is desirable to ensure that it cannot inadvertently be removed from the control wire slot 600. Accordingly, in the present embodiment the ball cavity 602 has a diameter sufficiently large to allow the ball 140 to pass therethrough while the wire cavity 604 is large enough to allow the control wire 118 to pass therethrough, but not large enough to allow the ball 140 pass therethrough. To assemble the control wire 118 with the yoke 204 according to the exemplary embodiment, the proximal end of wire 140 is inserted into the ball cavity 602 until the ball bottoms out, and then the control wire 118 is rotated until it is seated in the control wire cavity 604, thus constraining further movement of the ball 140. According to the present embodiment, the yoke 204 may be made of a biocompatible metal such as stainless steel or a high strength polymer such as Ultem™.

According to embodiments of the present invention, the clipping device 100 may be scaled to fit the requirements of different surgical procedures. In one exemplary embodiment, the clipping device 100 may be sized to fit through an endoscope having a working channel diameter of approximately 0.110 inches. The exemplary bushing may have a length of about 0.22 inches and an OD of approximately 0.085 inches. The capsule may have a length of about 0.5 inches, an OD of about 0.085 inches, and a wall thickness of about 0.003 inches. When assembled, the rigid length of the capsule 200 and the bushing 202 is approximately 0.625 inches. This length is important because if it is too great, the assembly will not pass through the bends of the flexible endoscope. In the exemplary clipping device, the outer sheath may have an ID of approximately 0.088 inches and an OD of about 0.102 inches. The overall length of the clipping device may be approximately 160 inches, while the tissue grasping portion of the clip arms 208 may be approximately 0.4 inches long.

Figure 30:
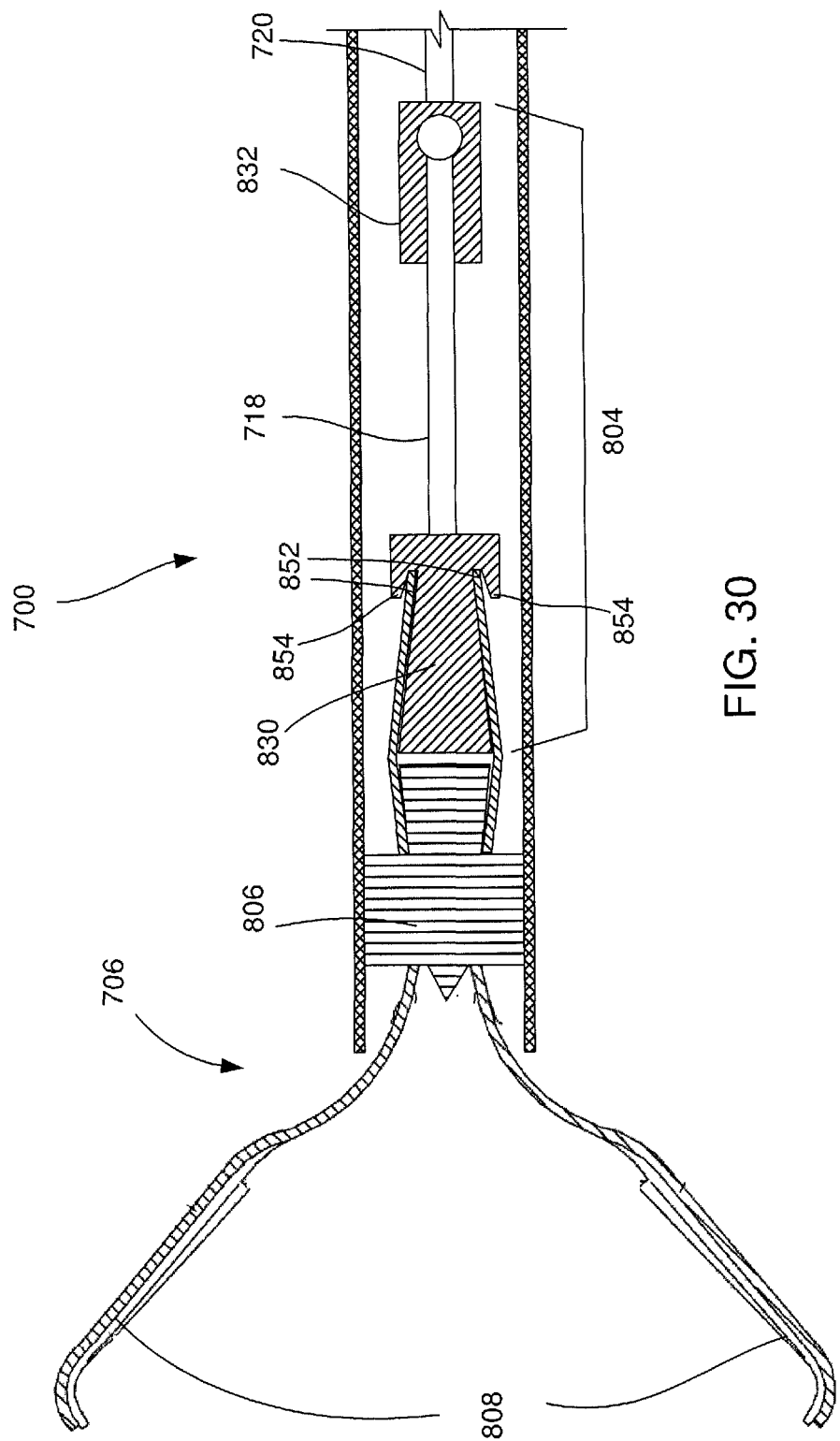
FIG. 30 shows a cross-sectional side view of a clipping device according to another embodiment of the present invention.
Figure 31:
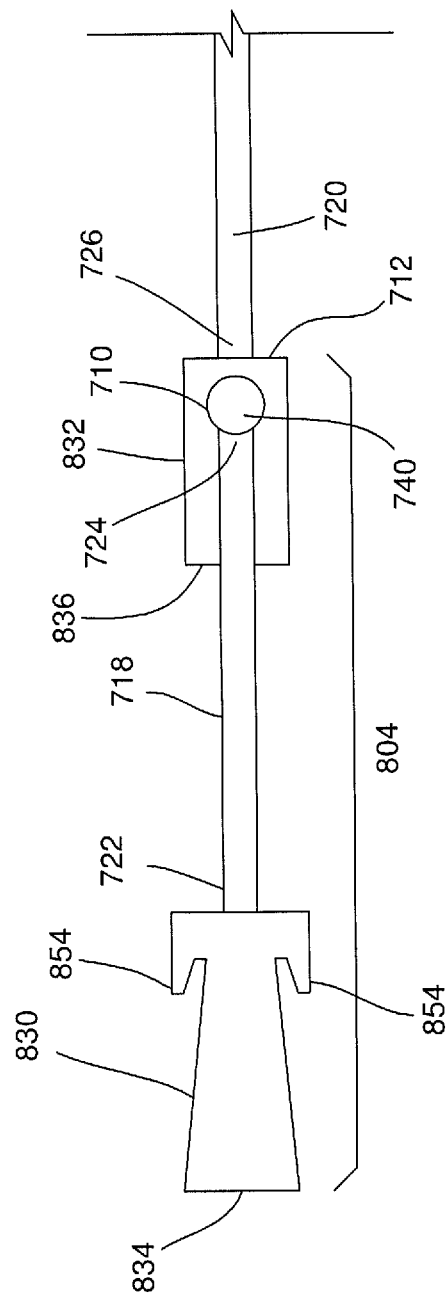
FIG. 31 shows a side view of a yoke and control wires attached thereto according to the embodiment of FIG. 30.

As shown in FIGS. 30-31, an alternate embodiment of a clipping device 700 comprises a clip assembly 706 connected to and movable via a handle assembly (not shown). The clipping device 700 is substantially similar to the clipping device 100 with a capsule 800 providing a structural shell for the clip assembly 706. The capsule 800 houses a yoke 804 and a tension member 806 for moving clip arms 808 coupled thereto, between open and closed configurations via movement of first and second control wires 718, 720. The yoke 804 is substantially similar to the yoke 204 of the clipping device 100, but includes a first portion 830 and a second portion 832 connected to one another via the first control wire 718.

The first control wire 718 is substantially similar to the control wire 118, except that an enlarged diameter portion (e.g., ball 740) is formed at a proximal end 724 thereof while the distal end 722 is coupled to the first portion 830. The ball 740 is releasably and rotatably received within the second portion 832. In a preferred embodiment, the distal end 722 is integrally formed with the first portion 830 with the first control wire 718 extending proximally therefrom. The proximal end 724, including the ball 740, may be mated with the second portion 832 by, for example, crimping the second portion 832 over the proximal end 724. As will be understood by those of skill in the art, the length of the first control wire 718 increases the extent of free space between proximal and distal ends of the yoke 804, thereby allowing additional structural support components at a distal end of the clipping device 700, while maintaining the rotatability of the device to prevent wind up of the second control wire 720.

The second control wire 720 extends longitudinally from a distal end 726 connected to the second portion 832 to a proximal end (not shown) connected to, for example, a spool (not shown) of a handle assembly. Similarly to the clipping device 100, the second control wire 720 may be moved distally and proximally to move the clip arms 808 between the open and the closed configurations. The second control wire 720 may be integrally formed with the second portion 832 such that the second control wire 720 extends proximally therefrom.

The first portion 830 may be formed substantially similarly to a distal portion of the yoke 204. The first portion 830 includes a yoke overhang 854 receiving proximal ends 852 of the clip arms 808. Similarly to the yoke 204, the first portion 830 also includes a connection mechanism at a distal end 834 thereof for releasably connecting to the tension member 806. The tension member 806 may be released from the yoke 804 upon exertion of a predetermined level of force in the same manner described above. The second portion 832 may be substantially similar to the proximal end of the yoke 204, including a socket 810 for receiving the ball 740 of the first control wire 718. The socket 710, however, is open to a distal end 836 of the second portion 832 to facilitate connection between the first and second portions 830, 832 via the first control wire 718.

It will be understood by those of skill in the art that the clipping device 700 may be used in substantially the same manner as described above in regard to the clipping device 100 with the same separate feedback indications to the user. Specifically, a first tactile feedback is provided to the user when the clip assembly 706 has been drawn proximally into the capsule 800 to a point beyond which further proximal movement of the clip assembly 706 into the capsule 800 will deploy the clip. A second tactile feedback is then provided when the first and second portions 830, 832 have been separated from one another locking the clip over the target tissue. A third tactile feedback provided to the user when the ball 740 of the first control wire 718 has been separated from the first portion 830 of the yoke 204 indicates that the clipping assembly 706 and the capsule 800 have been separated from the device 700.

The handle assembly, which may include a handle body and spool longitudinally movable along the handle body, is used to move the clip arms 808 between the open and the closed configuration in the same manner indicated above. Specifically, the spool, which is connected to a proximal end of the second control wire 820 may be moved relative to the handle body to move the clip arms 808 between the open and closed configurations. Application to the second control wire 720 of a proximally directed force greater than a threshold level deploys the clip assembly 706 separating the clip assembly 706 from a remaining portion of the clipping device 700, as described above in regard to the clipping device 100.

Figure 33:
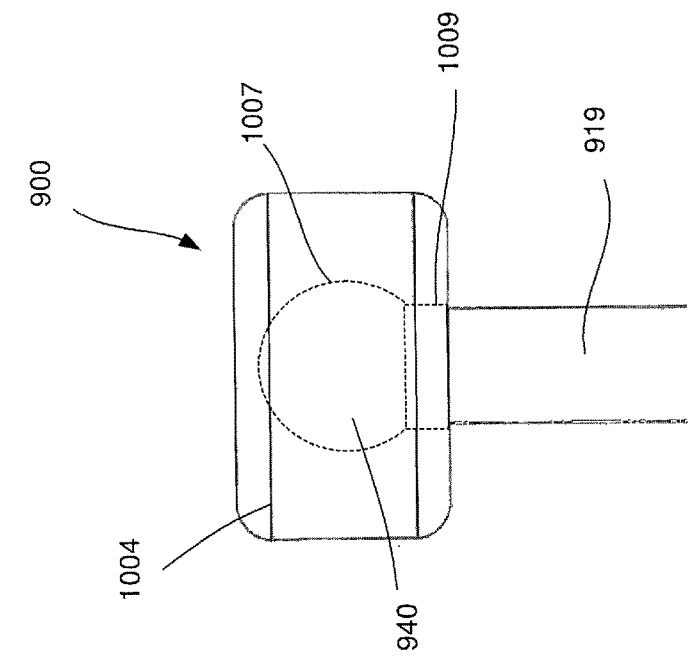
FIG. 33 shows a second cross-sectional side view of the control wire and yoke assembly shown in FIG. 32.
Figure 32:
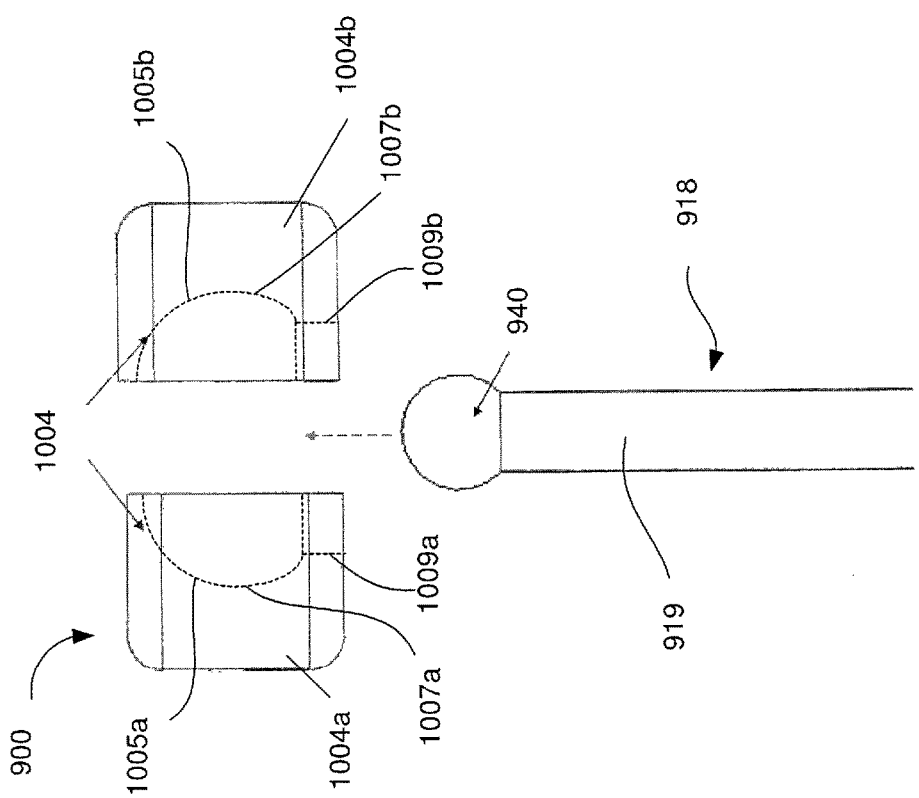
FIG. 32 shows a first cross-sectional side view of a control wire and yoke assembly according to another embodiment of the present invention.

According to another embodiment, as shown in FIGS. 32-33, a control wire and yoke assembly 900 are substantially similar to the assembly described above in regard to the control wire 118 and the yoke 204 of the device 100, comprising a control wire 918 and a yoke 1004 couplable with one another. The control wire 918 includes a wire portion 919 and a ball 940 at a distal end thereof. The control wire 918 and the yoke 1004 are substantially similar to the control wire 118 and the yoke 204 described, above, but are coupled together in a different a manner. In particular, the yoke 1004 is formed of a first component 1004a and a second component 1004b joined together to encapsulate the ball 940 of the control wire 918 and permit free rotation of the control wire 918 relative to the yoke 1004 about a longitudinal axis of the control wire 918. Free rotation of the control wire 918 relative to the yoke 1004 permits the clipping device to function as desired, without binding. Although the yoke 1004 is not shown as including any specific surface features, it will be understood by those of skill in the art that the yoke 1004 may include any of a variety of desired surface features as described above, such as, for example, a yoke overhang for receiving proximal ends of clip arms and/or a portion for joining the yoke 1004 to a tension member, as described above in regard to the embodiments above. It will be understood by those of skill in the art that the control wire and yoke assembly 900 may be used in place of the control wire and yoke assemblies described above in regard to the to the clip devices 100, 700.

As shown in FIG. 32, the first and second components 1004a, 1004b include recess portions 1005a, 1005b, respectively, which, when the first and second components 1004a and 1004b are joined to one another, form a cavity sized and shaped to rotatably retain the ball 940 of the control wire 918 therein. The first and second components 1004a, 1004b may, for example, be substantially symmetrical to one another about a longitudinal axis of the assembly 900 and may be joined to one another along a surface parallel to the longitudinal axis. When assembled, the recess portion 1005a of the first component 1004a faces the recess portion 1005b of the second component 1004b with the first and second recess portions 1005a , 1005b including first parts 1007a, 1007b, respectively, for accommodating the ball 940 and second parts 1009a ,1009b, respectively, for accommodating a portion of the wire 919 extending proximally from the ball 940. The first parts 1007a, 1007b are concave and, for example, substantially hemispherical while the second parts 1009a, 1009b each form, for example a part of a cylinder with a diameter less than that of the first portions 1007a and b.Thus, when the first and second components 1004a, 1004b of the yoke 1004 are joined together with the ball 940 received between the recess portions 1005a, 1005b thereof, as shown in FIG. 33, the first parts 1007a, 1007b form a cavity 1007 which is partially spherical for housing the ball 940 and the second parts 1009a, 1009b form a substantially cylindrical opening 1009 for accommodating the wire portion 919 extending from the ball 940. A diameter of the cavity 1007 is selected to be larger than a diameter of the ball 940 such that the ball 940 is freely rotatable therein. The first and second components 1004a, 1004b of the yoke 1004 may be bonded to one another using any known bonding/attachment mechanism such as, for example, ultrasonic welding and adhesive bonding. The first and second components 1004a, 1004b may be formed of a material such as metal, plastic, or any other material known to those in the field.

Figure 35:
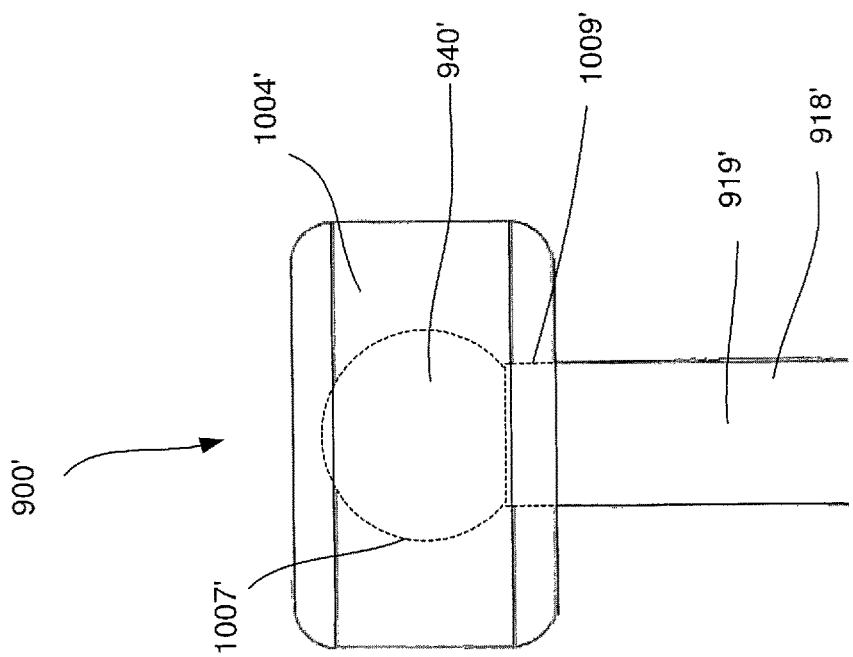
FIG. 35 shows a second cross-sectional side view of the control wire and yoke assembly shown in FIG. 34.
Figure 34:
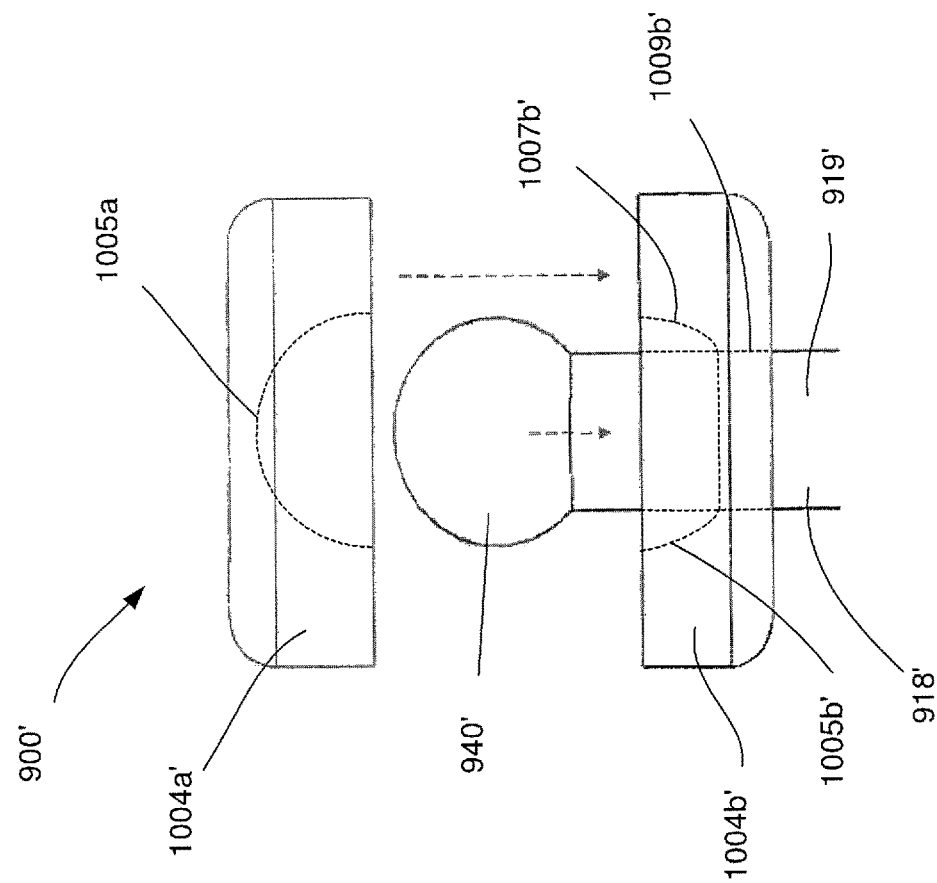
FIG. 34 shows a cross-sectional side view of a control wire and yoke assembly according to yet another embodiment of the present invention.

In an alternate embodiment, as shown in FIGS. 34-35, an assembly 900' may be substantially similar to the assembly 900 described above, comprising a yoke 1004' and a control wire 918'. The yoke 1004', however, is divided into first and second components 1004a', 1004b' substantially perpendicular to a longitudinal axis thereof. Thus, as shown in FIG. 34, a recess 1005a' of the first component 1004a' may be concave and substantially hemispherical while an interior surface 1005b' of the second component 1004b' includes a sloped portion 1007b' sized and shaped to seat the ball 940' therein and an opening 1009' extending therethrough from the first sloped portion 1007b' to an exterior surface 1011' of the second component 1004b' for accommodating a wire portion 919' of the control wire 918' extending proximally from the ball 940'. The opening 1009' is thus sized and shaped to slidably receive the wire portion 919' while preventing the ball 940' from passing therethrough. When the first and second components 1004a', 1004b' are joined to one another, as shown in FIG. 35, the ball 940' is encapsulated in a cavity 1007 formed by the recess portions 1005a', 1005b' and permitted to freely rotate therein. Thus, the first and second components 1004a', 1004b' are joined together, such that the control wire 918' is freely rotatable about a longitudinal axis thereof.

Figure 36:
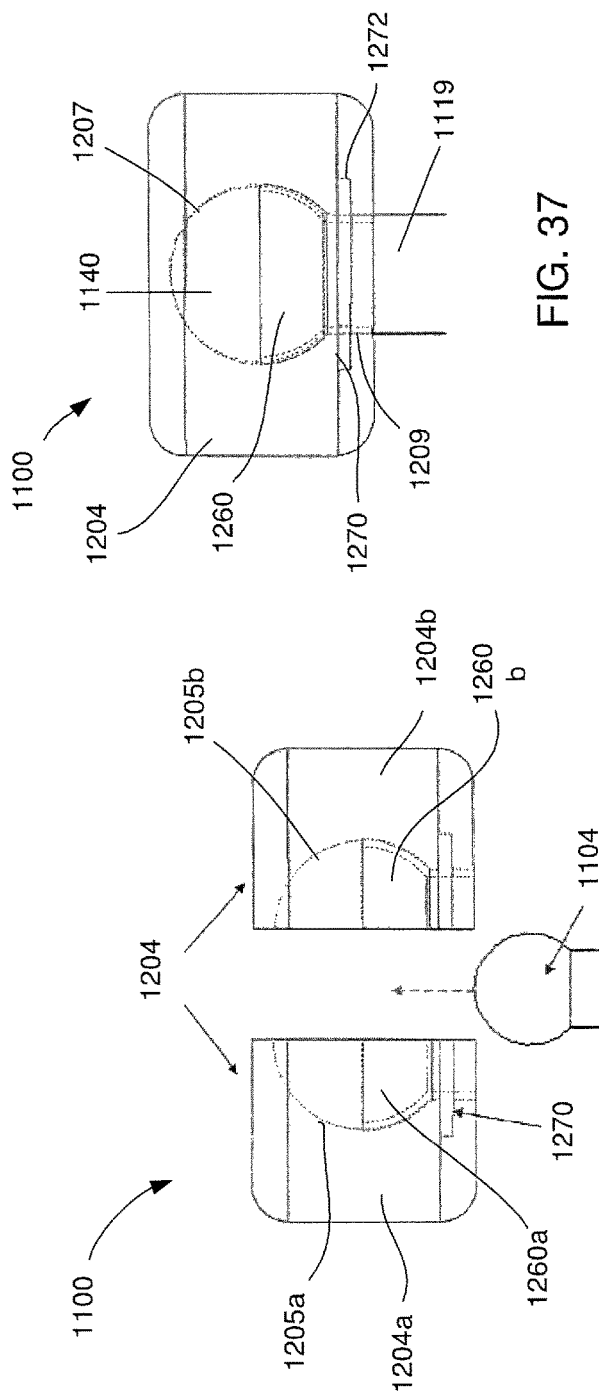
FIG. 36 shows a cross-sectional side view of a control wire and yoke assembly according to yet another embodiment of the present invention.
Figure 38:
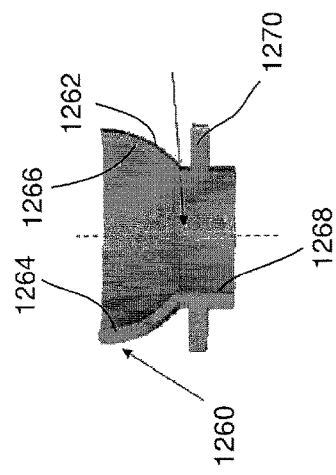
FIG. 38 shows a partial cross-sectional view of an insert for the assembly of FIG. 36.
Figure 37:
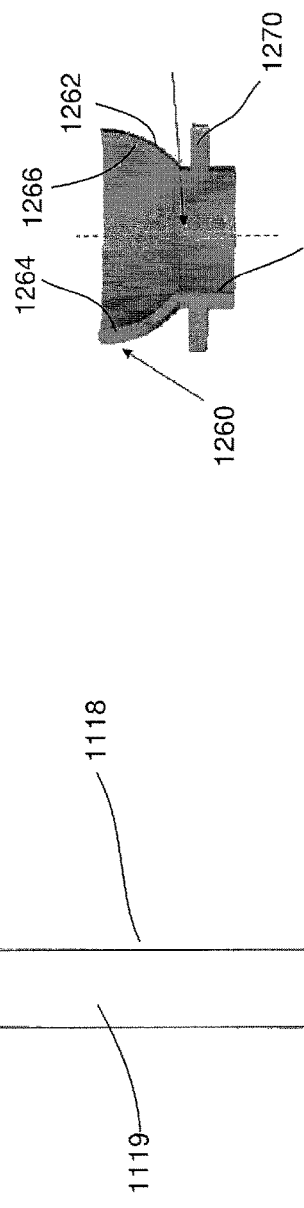
FIG. 37 shows a second cross-sectional side view of the control wire and yoke assembly shown in FIG. 36.

According to a further embodiment, as shown in FIGS. 36-38, an assembly 1100 is substantially similar to the assembly 900, comprising a ball 1140 at an end of a control wire 1118 that is encapsulated between first and second components 1204a, 1204b of a yoke 1204. The assembly 1100, however, further comprises an insert 1260 formed of a first and second element 1260a, 1260b each of which is configured for insertion into recess portions 1205a, 1205b of the first and second components 1204a, 1204b, respectively, so that the ball 1140 is seated in the insert 1260 between the first and second components 1204a, 1204b. The first and second components 1204a, 1204, and thereby the first and second elements of the insert 1260a, 1260b, are joined together around the ball 1140 of the control wire 1118 to permit free rotation thereof relative to the yoke 1204. The insert 1260 is formed of a material stronger than a material of which the yoke 1204 is formed so that the insert 1260 may provides support for devices in which a break mechanism of the control wire 1118—e.g., a reduced diameter section of a control wire designed to fail when a predetermined tension is applied thereto—requires a tension greater than that which the material of the yoke 1204 can withstand.

When the first and second elements 1260a, 1260b of the insert 1260 are joined to one another, as shown in FIG. 38, an exterior surface 1262 of the insert 1260 corresponds, for example, to a shape of a cavity 1007 formed by the recesses 1205a, 1205b. The exterior surface 1260 further includes an annular flange 1270 extending radially outward therefrom to engage a corresponding groove 1272 in each of the recesses 1005a, 1005b of the first and second components 1204a, 1204b such that the first and second elements 1260a, 1260b of the insert 1260 may be press-fit into the first and second components 1204a, 1204b, respectively. Although the assembly 1100 is specifically shown and described as including the annular flange 1270 and the corresponding groove 1272, it will be understood by those of skill in the art that any of a variety of elements may be employed to facilitate attachment between the first and second elements 1260a, 1260b of the insert and the first and second components 1204a,1204b.

An interior surface 1264, when the first and second elements 1260a, 1260b are joined to one another, includes a portion 1266 for seating the ball 1140 and an opening 1268 sized to permit the wire portion 1119 of the control wire 1118 to pass therethrough. The portion 1266 for seating the ball 1140 is, in this embodiment, substantially hemispherical, corresponding to a shape of at least a portion of the ball 1140. The opening 1268 is sized and shaped to permit the wire portion 1119 to extend therethrough while preventing the ball 1140 from passing therethrough. Thus, when the first and second components 1204a, 1204b,and thereby the first and second elements 1260a,1260b,are joined to one another, the ball 1140 is encapsulated between the first and second components 1204a, 1204b and seated within the portion 1266 of the insert 1260, permitting the control wire 1118 to freely rotate about a longitudinal axis thereof relative to the yoke 1204 and the insert 1260.

In an alternative embodiment, the insert 1260 may be formed of a single element rather than the first and second elements 1260a,1260b.In such an embodiment, the ball 1140 of the control wire is first seated within the concave portion 1266 with the wire portion 1119 extending through the opening 1268. The control wire 1118 and insert 1260 combination may then be encapsulated between the first and second components 1204a, 1204b.

The present invention has been described with reference to specific exemplary embodiments. Those skilled in the art will understand that changes may be made in details, particularly in matters of shape, size, material and arrangement of parts without departing from the teaching of the invention. For example, different shapes of the yoke, the tension member and the bushing may be used, and different attachments of the clip arms and control wire may be employed. Accordingly, various modifications and changes may be made to the embodiments without departing from the broadest scope of the invention as set forth in the claims that follow. The specifications and drawings are, therefore, to be regarded in an illustrative rather than a restrictive sense.

What is claimed is:

1. An apparatus for deployment of a hemostatic clip, comprising:
    a handle assembly;

a shaft connected to a distal portion of the handle assembly;

a clip assembly releasably coupled to a distal portion of the shaft, the clip assembly including:
  a capsule releasably coupled to the shaft;
  clip arms slidably received within the capsule and cooperating with the capsule to provide a first user feedback indicating a decision configuration of the clip assembly; and
  a yoke slidably received within the capsule, the yoke including proximal and distal portions releasably and rotatably connected to one another via a first control wire, a distal end of the distal portion being connected to proximal ends of the clip arms; and a second control wire extending from the handle assembly and coupled to a proximal end of the proximal portion of the yoke to move the clip assembly between open and closed configurations.

2. The apparatus according to claim 1, wherein the first control wire includes a ball connector at a proximal end thereof, the ball connector being coupled to the proximal portion of the yoke, separation of the first control wire from the proximal portion of the yoke separating the proximal and distal portions of the yoke from one another and providing a second user feedback.

3. The apparatus according to claim 2, wherein the first control wire further comprises a reduced diameter section adjacent to the ball connector, the reduced diameter section yielding when a tension in the control wire reaches a predetermined yield tension.

4. The apparatus according to claim 2, wherein the proximal portion of the yoke includes a ball cavity configured to retain the ball connector of the first control wire therein until a tension in the control wire reaches a predetermined yield tension.

5. The apparatus according to claim 3, wherein the yield tension is between approximately 10 lbf and 20 lbf.

6. The apparatus according to claim 1, further comprising:
  an over sheath movable between a first position covering the shaft and the clip assembly and a second position uncovering the clip assembly.

7. The apparatus according to claim 1, further comprising:
  a tension member releasably connected between the distal portion of the yoke and the clip arms and biasing the clip arms toward an open configuration, wherein the tension member releases from the yoke when the second control wire is moved proximally beyond the position at which the first user feedback is provided.

8. The apparatus according to claim 7, wherein the tension member and the yoke are releasably connected to one another by mating male and female C section members.

9. The apparatus according to claim 7, wherein separation of the yoke from the tension member occurs by one of fracture and deformation of the male C section member.

10. The apparatus according to claim 7, wherein separation of the yoke from the tension member occurs when a tension on the first control wire tension is at least a predetermined separation tension.

11. The apparatus according to claim 10, wherein the separation tension is at least approximately 4 lbf.

12. The apparatus according to claim 10, wherein the separation tension is less than approximately 12 lbf.

13. The apparatus according to claim 7, wherein separation of the yoke from the tension member locks the clip arms in a closed configuration by sliding the tension member and the clip arms proximally within the capsule.

14. The apparatus according to claim 7, wherein distal movement of the control wire, before separation of the yoke from the tension member, slides the clip arms distally out of the capsule into an open configuration.

15. A flexible clip deployment apparatus insertable to locations within a body through an endoscope, comprising:
  an elongated member extending from a proximal end to a distal end, the elongated member being flexible to be inserted to a target location via a natural body lumen;
  a bushing coupled to the distal end of the elongated member;
  a capsule releasably connected to the bushing;
  clip arms slidable within the capsule between open and closed configurations, the clip arms cooperating with the capsule to provide a first user feedback indicating a decision configuration of a clip assembly;
  a tension member coupled to the clip arms, the tension member biasing the clip arms toward the open configuration;
  a yoke slidably received within the capsule, the yoke including distal and proximal portions releasably connected to one another via a first control wire, a distal end of the distal portion being coupled to proximal ends of the clip arms; and
  a second control wire extending distally from a handle assembly to couple to the proximal portion of the yoke, distal movement of the second control wire within the elongated member moving the clip assembly distally relative to the capsule moving the clip arms to the open configuration, proximal movement of the control wire drawing the clip arms into the capsule to the closed configuration.

16. The apparatus according to claim 15, wherein a proximal end of the first control wire includes a ball connector rotatably received in the proximal portion of the yoke, the ball connector being detachable from a remaining length of the first control wire to provide a second user feedback indicating separation of the clip assembly from the shaft.

17. The apparatus according to claim 16, wherein the proximal portion of the yoke includes a ball cavity accommodating the ball connector of the first control wire.

18. The apparatus according to claim 16, wherein proximal movement of the second control wire beyond a point at which the clip assembly is in the decision configuration results in separation of the yoke from the tension member.

* * * * *